United States Patent
Walton et al.

(10) Patent No.: US 9,757,345 B2
(45) Date of Patent: Sep. 12, 2017

(54) NUTRITIONAL COMPOSITIONS INCLUDING CALCIUM BETA-HYDROXY-BETA-METHYLBUTYRATE, PROTEIN AND LOW LEVELS OF ELECTROLYTES

(71) Applicant: ABBOTT LABORATORIES, Abbott Park, IL (US)

(72) Inventors: Joseph Walton, Westerville, OH (US); Emily Stepp, Gahanna, OH (US); Amy Devitt-Maicher, Gahanna, OH (US); David Wolf, Worthington, OH (US); Vikkie Mustad, Galena, OH (US); Jeffrey Baxter, Westerville, OH (US); Terrence Mazer, New Albany, OH (US); Amy Marchio, Centerburg, OH (US)

(73) Assignee: ABBOTT LABORATORIES, Abbott Park, IL (US)

( * ) Notice: Subject to any disclaimer, the term of this patent is extended or adjusted under 35 U.S.C. 154(b) by 33 days.

(21) Appl. No.: 14/430,046

(22) PCT Filed: Sep. 20, 2013

(86) PCT No.: PCT/US2013/061014
§ 371 (c)(1),
(2) Date: Mar. 20, 2015

(87) PCT Pub. No.: WO2014/047497
PCT Pub. Date: Mar. 27, 2014

(65) Prior Publication Data
US 2015/0246011 A1    Sep. 3, 2015

Related U.S. Application Data

(60) Provisional application No. 61/703,965, filed on Sep. 21, 2012, provisional application No. 61/703,967, filed on Sep. 21, 2012.

(51) Int. Cl.
A61K 31/19 (2006.01)
A61K 36/889 (2006.01)
(Continued)

(52) U.S. Cl.
CPC ................ *A61K 31/19* (2013.01); *A23L 2/38* (2013.01); *A23L 2/66* (2013.01); *A23L 33/12* (2016.08);
(Continued)

(58) Field of Classification Search
None
See application file for complete search history.

(56) References Cited

U.S. PATENT DOCUMENTS 5,028,440 A     7/1991  Nissen
8,916,217 B2 *  12/2014 Johns ........................ A23L 1/30
                                                             426/106
2004/0176449 A1   9/2004  Abraham et al.

FOREIGN PATENT DOCUMENTS

CH    WO 2005002602 A2 *  1/2005  ............. A61K 35/20
CN        101785566 A       7/2010
(Continued)

OTHER PUBLICATIONS

Geraedts et al. (Intraduodenal administration of intact pea protein effectively reduces food intake in both lean and obese male subjects, PLoS One 2011; 6(9):e24878; Published online Sep. 13, 2011).*
(Continued)

*Primary Examiner* — Robert A Wax
*Assistant Examiner* — Melissa Mercier
(74) *Attorney, Agent, or Firm* — Porter Wright Morris & Arthur LLP

(57) ABSTRACT

Disclosed are nutritional compositions, and methods of using and making the nutritional compositions, that include calcium beta-hydroxy-beta-methylbutyrate and protein. The
(Continued)

calcium beta-hydroxy-beta-methylbutyrate is in sequestered or ion-exchanged form to reduce the interaction of the calcium with the protein in the nutritional composition and improve the overall stability of the nutritional composition.

21 Claims, 7 Drawing Sheets

(51) Int. Cl.

| | |
|---|---|
| *A61K 38/01* | (2006.01) |
| *A61K 31/202* | (2006.01) |
| *A61K 31/22* | (2006.01) |
| *A61K 33/00* | (2006.01) |
| *A61K 33/42* | (2006.01) |
| *A61K 36/28* | (2006.01) |
| *A61K 36/286* | (2006.01) |
| *A61K 36/31* | (2006.01) |
| *A61K 36/48* | (2006.01) |
| *A61K 9/00* | (2006.01) |
| *A23L 2/38* | (2006.01) |
| *A23L 2/66* | (2006.01) |
| *A61K 31/7004* | (2006.01) |
| *A61K 31/736* | (2006.01) |
| *A61K 33/06* | (2006.01) |
| *A61K 36/899* | (2006.01) |
| *A61K 38/28* | (2006.01) |
| *A23L 33/12* | (2016.01) |
| *A23L 33/16* | (2016.01) |
| *A23L 33/18* | (2016.01) |
| *A23L 33/185* | (2016.01) |
| *A23L 33/19* | (2016.01) |
| *A23L 33/21* | (2016.01) |

(52) U.S. Cl.
CPC .............. *A23L 33/16* (2016.08); *A23L 33/18* (2016.08); *A23L 33/185* (2016.08); *A23L 33/19* (2016.08); *A23L 33/21* (2016.08); *A61K 9/0095* (2013.01); *A61K 31/202* (2013.01); *A61K 31/22* (2013.01); *A61K 31/7004* (2013.01); *A61K 31/736* (2013.01); *A61K 33/00* (2013.01); *A61K 33/06* (2013.01); *A61K 33/42* (2013.01); *A61K 36/28* (2013.01); *A61K 36/286* (2013.01); *A61K 36/31* (2013.01); *A61K 36/48* (2013.01); *A61K 36/889* (2013.01); *A61K 36/899* (2013.01); *A61K 38/011* (2013.01); *A61K 38/018* (2013.01); *A61K 38/28* (2013.01); *A23V 2002/00* (2013.01)

(56) References Cited

FOREIGN PATENT DOCUMENTS

| | | |
|---|---|---|
| WO | 99/66917 A2 | 12/1999 |
| WO | 2005/102301 A2 | 11/2005 |
| WO | 2011/156238 A1 | 12/2011 |
| WO | 2014/047493 A1 | 3/2014 |

OTHER PUBLICATIONS

Pehrsson et al. (The Mineral Content of US Drinking and Municipal Water, accessed online Aug. 15, 2016).*
International Search Report and Written Opinion for PCT/US2013/061014 dated Feb. 6, 2014.
International Preliminary Report on Patentability for PCT/US2013/061014 dated Mar. 24, 2015.
Communication Pursuant to Rules 161(1) & 162 EPC for EP 13771718.7 dated May 18, 2015.
Written Opinion in Singapore Patent Application No. 11-2015-02205S dated Jan. 27, 2016.
Alon et al., "Supplementing with beta-hydroxy-beta-methylbutyrate (HMB) to build and maintain muscle mass: A review," Research Communications in Molecular Pathology and Pharmacology, PJD Publications, LTD (US), vol. 111, No. 1-4, Jan. 1, 2002, pp. 139-151.
Anonymous, "HMB (beta-hydroxy-beta-methylbutyrate): A scientific review," http://abbottnutrition.com/downloads/resourcecenter/hmb-a-scientific-review.pdf (Apr. 1, 2010).
Marcora et al., "Dietary treatment of rheumatoid cachexia with beta-hydroxy-beta-methylbutyrate, glutamine and arginine: A randomised controlled trial," Clinical Nutrition, Churchill Livingstone, London, GB, vol. 24, No. 3, Jun. 2005, pp. 442-454.
Office Action in Chinese Patent Application No. 201380060521.X dated Mar. 4, 2016.

* cited by examiner

| Assay | Interval | Sample 1, low K (450 mg) | Sample 2, high K (650 mg) | Sample 3, low K (450 mg) | Sample 4, high K (650 mg) | Sample 5, mid K (500 mg) | Sample 6, mid K (500 mg) |
|---|---|---|---|---|---|---|---|
| | | 0201 | 0202 | 0301 | 0302 | 0401 | 0701 |
| Agtron Color | 0D | 38.9 | 37.6 | 44.8 | 44.9 | 49.8 | N/A |
| | 1M | 36.3 | 33.8 | N/A | N/A | N/A | N/A |
| | 3M | N/A | N/A | 35.2 | 35.1 | N/A | N/A |
| Hunter Lab — L | 0D | ------ | ------- | 80.22 | 79.42 | 79.33 | 85.06 |
| | 1M | ------ | ------- | ------- | ------- | ------- | 82.67 |
| | 3M | ------ | ------ | 75.05 | 75.53 | ------- | 80.71 |
| | 6M | ------ | ------ | ------- | -------- | ------- | 80.00 |
| | 9M | ----- | ----- | ---- | ---- | ---- | ---- |
| Hunter Lab — a | 0D | ---- | ---- | -0.09 | 1 | 4.02 | -0.96 |
| | 1M | ---- | ---- | ---- | ---- | ---- | 0.33 |
| | 3M | ---- | ---- | 2.75 | 2.63 | ---- | 0.72 |
| | 6M | ---- | ---- | ---- | ---- | ---- | 1.06 |
| | 9M | ---- | ---- | ---- | ---- | ---- | ---- |
| Hunter Lab — b | 0D | ---- | ---- | 18.33 | 17.56 | 14.09 | 15.24 |
| | 1M | ---- | ---- | ---- | ---- | ---- | 16.34 |
| | 3M | ---- | ---- | 20.21 | 20.16 | ---- | 16.74 |
| | 6M | ---- | ---- | ---- | ---- | ---- | 17.57 |
| | 9M | ---- | ---- | ---- | ---- | ---- | ---- |
| Bound Sediment (MM) | 1M | 2 | 2 | ---- | ---- | ---- | 4 |
| | 3M | ---- | ---- | 11 | 5 | ---- | 8 |
| | 6M | ---- | ---- | ---- | ---- | ---- | 11 |
| | 9M | ---- | ---- | ---- | ---- | ---- | ---- |
| Bound Sediment (Rating) | 1M | 5 | 5 | ---- | ---- | ---- | 5 |
| | 3M | ---- | ---- | 6 | 6 | ---- | 6 |
| | 6M | ---- | ---- | ---- | ---- | ---- | 6 |
| | 9M | ---- | ---- | ---- | ---- | ---- | ---- |
| Cream | 1M | 1 | 1 | ---- | ---- | ---- | 1 |
| | 3M | ---- | ---- | 2 | 2 | ---- | 1 |
| | 6M | ---- | ---- | ---- | ---- | ---- | 2 |
| | 9M | ---- | ---- | ---- | ---- | ---- | ---- |
| Gel | 1M | 2 | 2 | ---- | ---- | ---- | 2 |
| | 3M | ---- | ---- | 2 | 3 | ---- | 3 |
| | 6M | ---- | ---- | ---- | ---- | ---- | 3 |
| | 9M | ---- | ---- | ---- | ---- | ---- | ---- |
| Grain | 0D | 1 | 1 | 1 | 1 | 1 | 1 |
| | 1M | 1 | 1 | ---- | ---- | ---- | 1 |
| | 3M | ---- | ---- | 1 | 1 | ---- | 1 |
| | 6M | ---- | ---- | ---- | ---- | ---- | ---- |
| | 9M | ---- | ---- | ---- | ---- | ---- | ---- |

FIG. 1A

| Assay | Interval | Sample 1, low K (450 mg) 0201 | Sample 2, high K (650 mg) 0202 | Sample 3, low K (450 mg) 0301 | Sample 4, high K (650 mg) 0302 | Sample 5, mid K (500 mg) 0401 | Sample 6, mid K (500 mg) 0701 |
|---|---|---|---|---|---|---|---|
| New Cream | 1M | 1 | 1 | ---- | ---- | ---- | 1 |
|  | 3M | ---- | ---- | 2 | 2 | ---- | 1 |
|  | 6M | ---- | ---- | ---- | ---- | ---- | 1 |
|  | 9M | ---- | ---- | ---- | ---- | ---- | ---- |
| pH | 0D | 6.53 | 6.54 | 6.36 | 6.41 | 6.59 | 6.65 |
|  | 1M | 6.51 | 6.56 | ---- | ---- | ---- | 6.59 |
|  | 3M | ---- | ---- | 6.32 | 6.37 | ---- | 6.56 |
|  | 6M | ---- | ---- | ---- | ---- | ---- | 6.52 |
|  | 9M | ---- | ---- | ---- | ---- | ---- | ----- |
| Sediment | 1M | 6 | 6 | ---- | ---- | ---- | 6 |
|  | 3M | ---- | ---- | 6 | 6 | ---- | 6 |
|  | 6M | ---- | ---- | ---- | ---- | ---- | 6 |
|  | 9M | ---- | ---- | ---- | ---- | ---- | ---- |
| Sediment (MM) | 1M | ---- | ---- | 11 | 6 | ---- | 5 |
|  | 3M | ---- | ---- | ---- | ---- | ---- | 8 |
|  | 6M | ---- | ---- | ---- | ---- | ---- | 12 |
|  | 9M | ---- | ----- | ----- | ---- | ---- | ----- |
| Unbound Sediment | 1M | 6F | 6F | ---- | ---- | ---- | 1 |
|  | 3M | ---- | ---- | 1 | 1 | ---- | 1 |
|  | 6M | ---- | ---- | ---- | ---- | ---- | 1 |
|  | 9M | ---- | ---- | ---- | ---- | ---- | ---- |
| Viscosity | 0D | 14.1 | 16.3 | 14.1 | 12.4 | 12.6 | 12.6 |
|  | 1M | 15.9 | 17.2 | ---- | ---- | ---- | 12.3 |
|  | 3M | ---- | ---- | 14 | 12.8 | ---- | 11.3 |
|  | 6M | ---- | ---- | ---- | ---- | ---- | 9.4 |
|  | 9M | ---- | ---- | ---- | ---- | ---- | ---- |
| Whey | 1M | 1 | 1 | 3 | 3 | ---- | 2 |
|  | 3M | ---- | ---- | ---- | ---- | ---- | 2 |
|  | 6M | ---- | ---- | ---- | ---- | ---- | 2 |
|  | 9M | ---- | ---- | ---- | ---- | ---- | ---- |
| Total Solids | 0D | 32.2 | 32.5 | 30.1 | 31.4 | 28.9 | 28.7 |

FIG. 1B

|  |  | Sample 7, Alginate Chelating @ 0.68% | Sample 8, Alginate Chelating @ 0.5% | Sample 9, Alginate Chelating @ 0.25% | Sample 10, Alginate Chelating @ 0.08% | Sample 11, Alginate Chelating @ 0.16% |
|---|---|---|---|---|---|---|
| Assay | Interval | 0104 | 0203 | 0303 | 0402 | 0403 |
| Agtron Color | 0D | 35.2 | 33.7 | 43.2 | N/A | N/A |
|  | 1M | 30.8 | 30.5 | N/A | N/A | N/A |
|  | 3M | N/A | N/A | 34.8 | N/A | N/A |
| Hunter Lab | L 0D | ------ | ------ | 79.35 | 80.03 | 80.20 |
|  | L 1M | ------ | ------ | ------ | ------ | ------ |
|  | L 3M | ------ | ------ | 75.13 | 76.73 | 80.01 |
|  | L 6M | ------ | ------ | 72.11 | 77.27 | 75.31 |
|  | L 9M | ----- | ----- | 71.20 | ---- | ---- |
|  | a 0D | ---- | ---- | -0.03 | 2.88 | 2.31 |
|  | a 1M | ---- | ---- | ---- | ---- | ---- |
|  | a 3M | ---- | ---- | 2.64 | 4.33 | 2.36 |
|  | a 6M | ---- | ---- | 3.11 | 2.27 | 3.58 |
|  | a 9M | ---- | ---- | 3.41 | ---- | ---- |
|  | b 0D | ---- | ---- | 18.72 | 14.07 | 14.24 |
|  | b 1M | ---- | ---- | ---- | ---- | ---- |
|  | b 3M | ---- | ---- | 20.64 | 16.71 | 17.29 |
|  | b 6M | ---- | ---- | 21.06 | 17.95 | 19.17 |
|  | b 9M | ---- | ---- | 21.57 | ---- | ---- |
| Bound Sediment (MM) | 1M | 1 | 1 | ---- | ---- | ---- |
|  | 3M | ---- | ---- | 5 | 6 | 6 |
|  | 6M | ---- | ---- | 7 | 13 | 8 |
|  | 9M | ---- | ---- | 7 | ---- | ---- |
| Bound Sediment (Rating) | 1M | 2 | 2 | ---- | ---- | ---- |
|  | 3M | ---- | ---- | 6 | 5 | 6 |
|  | 6M | ---- | ---- | 6 | 6 | 5 |
|  | 9M | ---- | ---- | 6 | ---- | ---- |
| Cream | 1M | 1 | 1 | ---- | ---- | ---- |
|  | 3M | ---- | ---- | 2 | 4 | 2 |
|  | 6M | ---- | ---- | 1 | 1 | 1 |
|  | 9M | ---- | ---- | 3 | ---- | ---- |
| Gel | 1M | 3 | 5 | ---- | ---- | ---- |
|  | 3M | ---- | ---- | 2 | 2 | 2 |
|  | 6M | ---- | ---- | 3 | 3 | 3 |
|  | 9M | ---- | ---- | 3 | ---- | ---- |

FIG. 2A

| Assay | Interval | Sample 7, Alginate Chelating @ 0.68% 0104 | Sample 8, Alginate Chelating @ 0.5% 0203 | Sample 9, Alginate Chelating @ 0.25% 0303 | Sample 10, Alginate Chelating @ 0.08% 0402 | Sample 11, Alginate Chelating @ 0.16% 0403 |
|---|---|---|---|---|---|---|
| Grain | 0D | 2VSP | 1 | 1VSP | 1 | 1 |
| | 1M | 1SP | 1 | ---- | ---- | ---- |
| | 3M | ---- | ---- | 1 | 1 | 1 |
| | 6M | ---- | ---- | 1 | 1 | 2 |
| | 9M | ---- | ---- | 1VSP | ---- | ---- |
| New Cream | 1M | 1 | 1 | ---- | ---- | ---- |
| | 3M | ---- | ---- | 2 | 3 | 1 |
| | 6M | ---- | ---- | 1 | ---- | ---- |
| | 9M | ---- | ---- | 1 | ---- | ---- |
| pH | 0D | 6.59 | 6.56 | 6.38 | 6.60 | 6.61 |
| | 1M | 6.58 | 6.54 | ---- | ---- | ---- |
| | 3M | ---- | ---- | 6.02 | 6.53 | 5.86 |
| | 6M | ---- | ---- | 6.32 | 6.49 | 5.61 |
| | 9M | ---- | ---- | 6.32 | ---- | ---- |
| Sediment | 1M | 5 | 5 | ---- | ---- | ---- |
| | 3M | ---- | ---- | 6 | 6 | 6 |
| | 6M | ---- | ---- | 6 | 6 | 6 |
| | 9M | ---- | ---- | 6 | ---- | ---- |
| Sediment (MM) | 1M | ---- | ---- | ---- | ---- | ---- |
| | 3M | ---- | ---- | 6 | 6 | 8 |
| | 6M | ---- | ---- | 8 | 14 | 10 |
| | 9M | ---- | ---- | 7 | ---- | ---- |
| Unbound Sediment | 1M | 1 | 1 | ---- | ---- | ---- |
| | 3M | ---- | ---- | 1 | 6D | 1 |
| | 6M | ---- | ---- | 1 | 1 | 6F |
| | 9M | ---- | ---- | 3A | ---- | ---- |
| Viscosity | 0D | 429.4 | 193.4 | 42.2 | 18.0 | 26.1 |
| | 1M | 261.9 | 323.9 | ---- | ---- | ---- |
| | 3M | ---- | ---- | 47.6 | 17.1 | 33.9 |
| | 6M | ---- | ---- | 44.8 | 14.1 | 95.8 |
| | 9M | ---- | ---- | 43.8 | ---- | ---- |
| Whey | 1M | 1 | 2 | ---- | ---- | ---- |
| | 3M | ---- | ---- | 3 | 3 | 2 |
| | 6M | ---- | ---- | 2 | 2 | 2 |
| | 9M | ---- | ---- | 2 | ---- | ---- |
| Total Solids | 0D | 32.0 | 32.6 | 31.4 | 28.7 | 28.3 |

FIG. 2B

| Assay | | Interval | Sample 12, Glycine @ 0.2% | Sample 13, Glycine @ 0.4% | Sample 14, Glucono delta Lactone @ 0.16% | Sample 15, Glucono delta Lactone @ 0.33% | Sample 16, Glucono delta Lactone @ 0.49% | Sample 17, Glucono delta Lactone @ 0.05% | Sample 18, Glucono delta Lactone @ 0.1% | Sample 19, Glucono delta Lactone @ 0.15% | Sample 20, Sodium Gluconate @ 0.36% |
|---|---|---|---|---|---|---|---|---|---|---|---|
| | | | 0704 | 0705 | 0204 | 0205 | 0206 | 0304 | 0305 | 0306 | 0207 |
| Agtron Color | | 0D | N/A | N/A | 39.6 | 40.4 | 38.9 | 46.2 | 45.6 | 46.2 | 38.9 |
| | | 1M | N/A | N/A | 36.9 | 36.0 | 34.9 | N/A | N/A | N/A | 36.0 |
| | | 3M | N/A | N/A | N/A | N/A | N/A | 35.1 | 39.6 | 40.7 | N/A |
| Hunter Lab | L | 0D | 84.37 | 84.03 | ---- | ---- | ---- | 81.13 | 81.18 | 81.48 | ---- |
| | | 1M | ---- | ---- | ---- | ---- | ---- | ---- | ---- | ---- | ---- |
| | | 3M | 79.70 | 79.05 | ---- | ---- | ---- | 77.24 | 78.86 | 79.48 | ---- |
| | | 6M | 78.73 | 78.20 | ---- | ---- | ---- | 75.00 | 76.93 | 77.57 | ---- |
| | | 9M | ---- | ---- | ---- | ---- | ---- | 74.92 | 75.81 | 76.79 | ---- |
| | a | 0D | -0.57 | -0.32 | ---- | ---- | ---- | -0.46 | -0.80 | -1.25 | ---- |
| | | 1M | ---- | ---- | ---- | ---- | ---- | ---- | ---- | ---- | ---- |
| | | 3M | 1.30 | 1.58 | ---- | ---- | ---- | 1.91 | 0.61 | -0.21 | ---- |
| | | 6M | 1.71 | 1.95 | ---- | ---- | ---- | 2.06 | 0.49 | -0.12 | ---- |
| | | 9M | ---- | ---- | ---- | ---- | ---- | 2.16 | 0.85 | 0.25 | ---- |
| | b | 0D | 15.57 | 15.91 | ---- | ---- | ---- | 18.10 | 18.72 | 18.68 | ---- |
| | | 1M | ---- | ---- | ---- | ---- | ---- | ---- | ---- | ---- | ---- |
| | | 3M | 17.58 | 18.03 | ---- | ---- | ---- | 20.14 | 19.84 | 19.70 | ---- |
| | | 6M | 18.43 | 18.83 | ---- | ---- | ---- | 20.68 | 20.58 | 20.64 | ---- |
| | | 9M | ---- | ---- | ---- | ---- | ---- | 20.89 | 21.31 | 21.32 | ---- |
| Bound Sediment (MM) | | 1M | ---- | ---- | 2 | 18 | 30 | ---- | ---- | ---- | 6 |
| | | 3M | 4 | 6 | ---- | ---- | ---- | 20 | 45 | 46 | ---- |
| | | 6M | 8 | 9 | ---- | ---- | ---- | 20 | 40 | 40 | ---- |
| | | 9M | ---- | ---- | ---- | ---- | ---- | 27 | 37 | 38 | ---- |
| Bound Sediment (Rating) | | 1M | ---- | ---- | 5 | 6 | 6 | ---- | ---- | ---- | 5 |
| | | 3M | 6 | 6 | ---- | ---- | ---- | 6 | 6 | 6 | ---- |
| | | 6M | 6 | 6 | ---- | ---- | ---- | 6 | 6 | 6 | ---- |
| | | 9M | ---- | ---- | ---- | ---- | ---- | 6 | 6 | 6 | ---- |
| Cream | | 1M | ---- | ---- | 1 | 1 | 1 | ---- | ---- | ---- | 1 |
| | | 3M | 1 | 1 | ---- | ---- | ---- | 2 | 2 | 2 | ---- |
| | | 6M | 3 | 3 | ---- | ---- | ---- | 2 | 3 | 4 | ---- |
| | | 9M | ---- | ---- | ---- | ---- | ---- | 6 | 6 | 6 | ---- |
| Gel | | 1M | ---- | ---- | 2 | 2 | 2 | ---- | ---- | ---- | 2 |
| | | 3M | 3 | 3 | ---- | ---- | ---- | 3 | 3 | 3 | ---- |
| | | 6M | 3 | 3 | ---- | ---- | ---- | 4 | 5 | 5 | ---- |
| | | 9M | ---- | ---- | ---- | ---- | ---- | 3 | 3 | 3 | ---- |
| Grain | | 0D | 1 | 1 | 1 | 1 | 1 | 1VSP | 3VSP | 3VSP | 1 |
| | | 1M | ---- | ---- | 1 | 1 | 1 | ---- | ---- | ---- | 1 |
| | | 3M | 1 | 1 | ---- | ---- | ---- | 1 | 1 | 3 | ---- |
| | | 6M | 1 | 1 | ---- | ---- | ---- | 1 | 1 | 1 | ---- |
| | | 9M | ---- | ---- | ---- | ---- | ---- | 2 | 2 | 2 | ---- |
| New Cream | | 1M | ---- | ---- | 1 | 1 | 1 | ---- | ---- | ---- | 1 |
| | | 3M | 1 | 1 | ---- | ---- | ---- | 2 | 2 | 2 | ---- |
| | | 6M | 4 | 3 | ---- | ---- | ---- | 3 | 2 | 2 | ---- |
| | | 9M | ---- | ---- | ---- | ---- | ---- | 5 | 5 | 5 | ---- |
| pH | | 0D | 6.63 | 6.64 | 6.45 | 6.20 | 6.04 | 6.31 | 6.25 | 6.18 | 6.47 |
| | | 1M | ---- | ---- | 6.37 | 6.19 | 6.06 | ---- | ---- | ---- | 6.45 |
| | | 3M | 6.57 | 6.56 | ---- | ---- | ---- | 6.22 | 6.21 | 6.14 | ---- |
| | | 6M | 6.52 | 6.52 | ---- | ---- | ---- | 6.26 | 6.19 | 6.12 | ---- |
| | | 9M | ---- | ---- | ---- | ---- | ---- | 6.26 | 6.19 | 6.11 | ---- |
| Sediment | | 1M | ---- | ---- | 6 | 6 | 6 | ---- | ---- | ---- | 6 |
| | | 3M | 6 | 6 | ---- | ---- | ---- | 6 | 6 | 6 | ---- |
| | | 6M | 6 | 6 | ---- | ---- | ---- | 6 | 6 | 6 | ---- |
| Sediment (MM) | | 1M | ---- | ---- | ---- | ---- | ---- | ---- | ---- | ---- | ---- |
| | | 3M | 7 | 7 | ---- | ---- | ---- | 22 | 45 | 46 | ---- |
| | | 6M | 12 | 10 | ---- | ---- | ---- | 22 | 42 | 42 | ---- |
| | | 9M | ---- | ---- | ---- | ---- | ---- | 26 | 37 | 39 | ---- |

FIG. 3A

|  |  | Sample 12, Glycine @ 0.2% | Sample 13, Glycine @ 0.4% | Sample 14, Glucono delta Lactone @ 0.16% | Sample 15, Glucono delta Lactone @ 0.33% | Sample 16, Glucono delta Lactone @ 0.49% | Sample 17, Glucono delta Lactone @ 0.05% | Sample 18, Glucono delta Lactone @ 0.1% | Sample 19, Glucono delta Lactone @ 0.15% | Sample 20, Sodium Gluconate @ 0.36% |
|---|---|---|---|---|---|---|---|---|---|---|
| Assay | Interval | 0704 | 0705 | 0204 | 0205 | 0206 | 0304 | 0305 | 0306 | 0207 |
| Unbound Sediment | 1M | ---- | ---- | 6F | 1 | 1 | ---- | ---- | ---- | 6F |
|  | 3M | 1 | 1 | ---- | ---- | ---- | 1 | 1 | 1 | ---- |
|  | 6M | 1 | 1 | ---- | ---- | ---- | 2C | 1 | 1 | ---- |
|  | 9M | ---- | ---- | ---- | ---- | ---- | 3A | 1 | 1 | ---- |
| Viscosity | 0D | 14.9 | 15.9 | 13.6 | 14.0 | 9.3 | 14.5 | 15.0 | 16.5 | 15.6 |
|  | 1M | ---- | ---- | 18.8 | 13.8 | 9.0 | ---- | ---- | ---- | 16.8 |
|  | 3M | 11.1 | 13.1 | ---- | ---- | ---- | 11.1 | 0.0 | 0.0 | ---- |
|  | 6M | 10.5 | 11.6 | ---- | ---- | ---- | 9.4 | 6.8 | 7.0 | ---- |
|  | 9M | ---- | ---- | ---- | ---- | ---- | 8.2 | 6.5 | 6.3 | ---- |
| Whey | 1M | ---- | ---- | 1 | 1 | 1 | ---- | ---- | ---- | 1 |
|  | 3M | 2 | 2 | ---- | ---- | ---- | 5 | 4 | 4 | ---- |
|  | 6M | 2 | 2 | ---- | ---- | ---- | 3 | 4 | 5 | ---- |
|  | 9M | ---- | ---- | ---- | ---- | ---- | 6 | 6 | 6 | ---- |
| Total Solids | 0D | 28.29 | 28.83 | 31.9 | 32.3 | 31.2 | 30.5 | 30.6 | 31.7 | 32.8 |

FIG. 3B

| Variable | Sequestrant | pH | Cream*, % w/w | Pellet*, % w/w | Soluble Ca*, mg/kg |
|---|---|---|---|---|---|
| Sample 1 | Control, low K (450 mg) | 6.53 | N/A | N/A | 479 |
| Sample 2 | Control, high K (650 mg) | 6.59 | N/A | N/A | 519 |
| Sample 8 | Alginate, 0.5% | 6.55 | N/A | N/A | 544 |
| Sample 14 | Glucono-Δ-lactone, 0.16% | 6.39 | N/A | N/A | 553 |
| Sample 15 | Glucono-Δ-lactone, 0.33% | 6.19 | N/A | N/A | 587 |
| Sample 16 | Glucono-Δ-lactone, 0.49% | 6.03 | N/A | N/A | 641 |
| Sample 20 | NaGluconate, 0.36% | 6.53 | N/A | N/A | 493 |
| Sample 5 | Control, low K (450 mg) | 6.6 | N/A | 16.5 | 293 |
| Sample 10 | Alginate, chelating, 0.08% | 6.6 | N/A | 19.2 | 321 |
| Sample 11 | Alginate, chelating, 0.16% | 6.6 | N/A | 20.4 | 335 |
| Sample 6 | Control | N/A | 7.8 | 17.3 | 458 |
| Sample 12 | 0.2% glycine | N/A | 7.8 | 16.8 | 419 |
| Sample 13 | 0.4% glycine | N/A | 7.9 | 16.9 | 361 |

FIG. 4

NUTRITIONAL COMPOSITIONS INCLUDING CALCIUM BETA-HYDROXY-BETA-METHYLBUTYRATE, PROTEIN AND LOW LEVELS OF ELECTROLYTES

CROSS REFERENCE TO RELATED APPLICATIONS

This application is the U.S. national stage entry of International Application No. PCT/US2013/061014, filed Sep. 20, 2013, which claims priority to and any benefit of U.S. Provisional Patent Application No. 61/703,965, filed Sep. 21, 2012 and U.S. Provisional Application No. 61/703,967, filed Sep. 21, 2012, the entire contents of which are incorporated by reference in their entirety.

FIELD OF THE DISCLOSURE

The present disclosure relates to nutritional compositions including calcium beta-hydroxy-beta-methylbutyrate and methods of using and manufacturing the same. More particularly, the present disclosure relates to nutritional compositions which may be in liquid form including calcium beta-hydroxy-beta-methylbutyrate that has been treated by sequestration (chelation), with an ion exchange resin/polymer, or both by sequestration (chelation) and with an ion exchange resin/polymer so as to render the calcium ions less soluble in the liquid compositions. The stability of such compositions is improved and the amount of any one of sodium, potassium, and phosphorus electrolytes in the compositions is reduced such that the compositions can be more suitably used by individuals with diabetes or chronic kidney dysfunction to build, maintain, or both build and maintain muscle mass.

BACKGROUND OF THE DISCLOSURE

Diabetes mellitus is a disorder of carbohydrate metabolism resulting from insufficient production of, or reduced sensitivity to, insulin. In persons who have diabetes, the normal ability of body cells to use glucose is inhibited, thereby increasing blood sugar levels. As more glucose accumulates in the blood, excess levels of sugar are excreted in the urine. Corresponding symptoms of diabetes include increased urinary volume and frequency, thirst, hunger, weight loss, and weakness.

There are two variations of diabetes. Type 1 diabetes is insulin dependent diabetes mellitus for which insulin administration is required. In a subject patient with type 1 diabetes, insulin is not secreted by the pancreas and therefore must be taken by injection or inhalation. Type 2 diabetes may be controlled by dietary restriction, oral anti-hyperglycemic agents, and/or insulin administration. Type 2 diabetes can be attributable to dilatory pancreatic secretion of insulin and reduced sensitivity to the action of insulin on target tissues. Individuals with diabetes and insulin resistance commonly suffer from muscle loss, muscle wasting, poor muscle quality and strength, and the inability to build new muscle mass in sufficient quantities.

In order to address these muscle wasting and muscle loss issues of diabetics, it is desirable for many diabetics to use, at least in part, nutritional solutions that include one or more protein sources to facilitate and stimulate muscle mass production and strength. Protein-containing nutritional products are available that are designed to increase muscle mass and reduce muscle wasting in individuals. Some of these nutritional products use calcium beta-hydroxy-beta-methylbutyrate (HMB) in combination with protein to further muscle building in the body. HMB is a metabolite of the amino acid leucine, and calcium HMB is the only source of HMB that is Generally Regarded As Safe (GRAS). Nutritional emulsions are particularly useful in this regard because such emulsions may contain a balance of protein, fat, carbohydrates, vitamins, and minerals that is useful for helping build and maintain healthy muscle.

Diabetes is the number one cause of chronic kidney dysfunction (impaired renal function) in individuals and many diabetic individuals also have impaired renal function. Individuals with this condition in later stages of renal failure must be very careful about their total intake of electrolytes such as potassium, sodium, and phosphorus, so as to not overburden their weakened kidneys. As a result, nutritional products including calcium HMB and protein have not been an option for many diabetics. This has been the case to date as nutritionals having calcium HMB and protein have generally required high levels of protein stabilizers, such as organic acid salts including sodium citrates, potassium citrates, sodium phosphates, and potassium phosphates. The high level of protein stabilizers has been required because the combination of calcium HMB and protein systems in liquid nutritionals has proven difficult to effectively stabilize over time as the soluble divalent calcium species in the liquid nutritional, much of which is derived from the calcium HMB, is highly reactive with the protein present in the system and leads to numerous unwanted issues, including undesirably high viscosities, phase separation, and protein aggregation that results in sedimentation, gelation, and/or coagulation defects in the resulting product. This is especially true for non-acidified shelf stable liquid beverages subjected to high heat, such as during a retort sterilization process for microbiological control. As such, without the required protein stabilizers to keep the protein present in the system from reacting with soluble calcium species and precipitating out of solution, a suitable commercial product cannot be formulated.

As such, there is a need for calcium HMB and protein-containing nutritional products, and specifically nutritional liquids, that are stable for a sufficiently long period of time and suitable for use by diabetics and diabetics with chronic kidney dysfunction to build and maintain muscle and muscle mass. Additionally, it would be beneficial if these liquid nutritionals including calcium HMB and protein could have low levels of at least one of potassium, sodium, and phosphorus to assist the user in balancing the dietary intake of electrolytes.

SUMMARY OF THE DISCLOSURE

The present disclosure is directed to stable nutritional compositions, and stable liquid nutritional emulsions in particular, that include calcium beta-hydroxy-beta-methylbutyrate (HMB) and at least one protein source. Such nutritional compositions including the liquid nutritional emulsions are often either retort or aseptically sterilized. The calcium HMB utilized in the nutritional compositions may be a sequestered calcium HMB such that the calcium HMB has been subjected to a sequestering process with a suitable sequestering agent prior to incorporation into the nutritional composition. As a result, the amount of soluble divalent calcium present in the nutritional system is substantially reduced and the stability of the composition is substantially increased as the protein-divalent calcium interactions in solution are limited. The calcium HMB utilized in the nutritional compositions may alternatively be, or additionally be, an ion-exchanged calcium HMB wherein at least a portion of the calcium ions have been exchanged and removed such that the amount of soluble calcium in the system is substantially reduced. This sequestered calcium HMB or ion-exchanged calcium HMB significantly reduces or eliminates the need for traditional organic acid salt protein stabilizers that are generally comprised of one or more sodium citrates, potassium citrates, sodium phosphates, and potassium phosphates. Consequently, the nutritional compositions can suitably be used by individuals with chronic kidney dysfunction and impaired renal function without concern of undesirable electrolyte overload. In some embodiments, the nutritional compositions may additionally include an inhibitor of electrolyte absorption to reduce the absorption of electrolytes into the body and further reduce the burden on the kidneys.

Along with the nutritional compositions disclosed herein, methods of using the nutritional compositions for building and maintaining muscle mass, as well as reducing muscle mass loss, are disclosed. Additionally, methods of manufacturing the sequestered calcium HMB and ion-exchanged calcium HMB are disclosed.

A liquid nutritional composition according to one exemplary embodiment comprises calcium beta-hydroxy-beta-methylbutyrate, protein, potassium in a concentration of less than 800 ppm, sodium in a concentration of less than 400 ppm, and phosphorus in a concentration of less than 500 ppm.

A liquid nutritional composition according to one exemplary embodiment comprises calcium beta-hydroxy-beta-methylbutyrate, protein, and potassium in a concentration of less than 800 ppm.

A liquid nutritional composition according to one exemplary embodiment comprises calcium beta-hydroxy-beta-methylbutyrate, protein, and sodium in a concentration of less than 400 ppm.

A liquid nutritional composition according to one exemplary embodiment comprises calcium beta-hydroxy-beta-methylbutyrate, protein, and phosphorus in a concentration of less than 500 ppm.

A method of reducing muscle loss in an individual with a metabolic disorder according to one exemplary embodiment is also disclosed. The method comprises administering to the individual with the metabolic disorder a liquid nutritional composition comprising calcium beta-hydroxy-beta-methylbutyrate, protein, potassium in a concentration of less than 800 ppm, sodium in a concentration of less than 400 ppm, and phosphorus in a concentration of less than 500 ppm.

A method of reducing muscle loss in an individual with diabetes according to one exemplary embodiment is also disclosed. The method comprises administering to the individual with diabetes a liquid nutritional composition comprising calcium beta-hydroxy-beta-methylbutyrate, protein, potassium in a concentration of less than 800 ppm, sodium in a concentration of less than 400 ppm, and phosphorus in a concentration of less than 500 ppm.

A method of reducing muscle loss in an individual with chronic kidney dysfunction according to one exemplary embodiment is also disclosed. The method comprises administering to the individual with chronic kidney dysfunction a liquid nutritional composition comprising calcium beta-hydroxy-beta-methylbutyrate, protein, potassium in a concentration of less than 800 ppm, sodium in a concentration of less than 400 ppm, and phosphorus in a concentration of less than 500 ppm.

It has been unexpectedly found that nutritional compositions, and specifically liquid nutritional compositions such as nutritional emulsions, can be manufactured including calcium HMB and protein in a form having long term stability, with acceptable viscosity, and suitability for use by people with diabetes or chronic kidney disease, by providing the calcium HMB in sequestered form into the nutritional composition. By first subjecting the calcium HMB to a food grade sequestering agent that is free or substantially free of sodium, potassium, and phosphorus, the divalent calcium ions can be sequestered/coordinated such that the amount of soluble divalent calcium ions in the resulting nutritional composition can be significantly decreased and the amount of organic acid salts comprised of one or more sodium citrates, potassium citrates, sodium phosphates, and potassium phosphates can be substantially reduced as they are not required to stabilize the protein present in the system. Because these organic acid salts are no longer required, the total respective amounts of sodium, potassium, and phosphorus in the resulting nutritional composition are substantially reduced such that the composition may be suitably used by people with metabolic disorders, including people with diabetes or chronic kidney dysfunction. The use of an inhibitor of electrolyte absorption may also further reduce the burden on the kidneys as described herein.

Additionally, it has also been discovered that nutritional compositions, and specifically liquid nutritional compositions, can be manufactured including calcium HMB and protein in a form having long term stability, with an acceptable viscosity, and suitability for use by people with diabetes or chronic kidney disease by utilizing calcium HMB that has been subjected to an ion-exchange resin or polymer prior to incorporation into the nutritional composition. By subjecting the calcium HMB to an ion-exchange resin or polymer prior to incorporation in the nutritional composition, the divalent calcium ions present can be exchanged and replaced with other less destructive ions, e.g., hydrogen, such that the amount of divalent calcium ions present in the nutritional composition is substantially reduced and the need for organic acid salts comprised of one or more sodium citrates, potassium citrates, sodium phosphates, and potassium phosphates is reduced or eliminated.

By providing a stable nutritional composition that includes both protein and calcium HMB and has reduced levels of potassium, sodium, and phosphorus, the present disclosure provides nutritional compositions that are safely useable by individuals with metabolic disorders, including individuals with diabetes or chronic kidney dysfunction. While the nutritional compositions are desirably liquid nutritional compositions such as nutritional emulsions, the present disclosure also provides alternative nutritional product forms including powders, bars, and the like. With the nutritional compositions disclosed herein, individuals with metabolic disorders can safely use the nutritional compositions to build and maintain muscle mass and to reduce muscle loss over time without concern of electrolyte overload.

BRIEF DESCRIPTION OF THE DRAWINGS

FIGS. 1A, 1B, 2A, 2B, 3A, and 3B are tables showing various physical and functional properties of the emulsions evaluated in Example 21.

FIG. 4 is a table showing binding affinity for calcium of the emulsions evaluated in Example 21.

DETAILED DESCRIPTION OF THE DISCLOSURE

The present disclosure is generally directed to nutritional compositions, including liquid nutritional emulsions, which include a sequestered or ion-exchanged calcium HMB in combination with protein and reduced levels of potassium, sodium, and phosphorus. By reducing the overall levels of potassium, sodium, and phosphorus, the nutritional compositions disclosed herein may be suitable for use by a wide variety of individuals, including those individuals with metabolic disorders who are sensitive to levels of electrolytes.

The present disclosure provides methods for solving longstanding problems with liquid nutritionals that include protein and calcium HMB, including precipitation, sedimentation, stability, electrolyte load, and viscosity issues. The present disclosure also provides the solutions to these problems without the use of traditional organic acid salts including one or more of sodium citrates, potassium citrates, sodium phosphates, and potassium phosphates which make many such products unsuitable for individuals with metabolic disorders. By using sequestration processes including, for example, sequestration by one or more of alginates, phytates, gluconic acid, and glycine, or ion-exchange processes, prior to incorporation of the calcium HMB into the liquid nutritional, alone or in combination with an inhibitor of electrolyte absorption, the amount of soluble divalent calcium available in the system is substantially reduced such that the interaction between the soluble calcium species and the protein present in the liquid matrix is also substantially reduced and unwanted precipitation and sedimentation is minimized or eliminated. The compositions of the present disclosure accomplish this without substantial use of unwanted electrolyte-containing materials that can be detrimental to a substantial population of the intended users.

These and other optional elements or limitations of the nutritional compositions and related methods, according to the present disclosure are described in further detail herein.

The term "calcium HMB" as used herein, unless otherwise specified, refers to the calcium salt of beta-hydroxy-beta-methylbutyrate (also referred to as beta-dydroxyl-3-methyl butyric acid, beta-hydroxy isovaleric acid, or HMB), which is most typically in a monohydrate form. All weights, percentages, and concentrations as used herein to characterize calcium HMB are based on the weight of calcium HMB monohydrate, unless otherwise specified.

The term "ion-exchanged calcium HMB" as used herein, unless other specified, refers to calcium HMB that has been subjected to an ion-exchange resin or ion-exchange polymer such that at least a portion of the divalent calcium present in the calcium HMB has been replaced with another ion.

The terms "fat" and "oil" as used herein, unless otherwise specified, are used interchangeably to refer to lipid materials derived or processed from plants or animals. These terms also include synthetic lipid materials so long as such synthetic materials are suitable for oral administration to humans.

The term "shelf stable" as used herein, unless otherwise specified, refers to a substantially nutritional liquid that remains commercially stable after being packaged and then stored at 18-24° C. for at least 3 months, including from about 6 months to about 24 months, and also including from about 12 months to about 18 months.

The terms "sterile," "sterilized," and "sterilization" as used herein, unless otherwise specified, refer to the reduction in transmissible agents such as fungi, bacteria, viruses, spore forms, and so forth, in food or on food grade surfaces to the extent necessary to render such foods suitable for human consumption. Sterilization processes may include various techniques involving the application of heat, peroxide or other chemicals, irradiation, high pressure, filtration, or combinations or variations thereof.

All percentages, parts, and ratios as used herein, are by weight of the total nutritional composition, unless otherwise specified. All such weights as they pertain to listed ingredients are based on the active level and, therefore, do not include solvents or by-products that may be included in commercially available materials, unless otherwise specified.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the present disclosure shall include the corresponding plural characteristics or limitations, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The various exemplary embodiments of the present disclosure may also be substantially free of any optional or selected ingredient or feature described herein, provided that the remaining nutritional compositions still contain all of the required ingredients or features as described herein. In this context, and unless otherwise specified, the term "substantially free" means that the selected nutritional composition contains less than a functional amount of the optional ingredient, typically less than 5% by weight, including less than 4% by weight, including less than 3% by weight, including less than 2% by weight, including less than 1% by weight, including less than 0.5% by weight, including less than 0.1% by weight, and also including zero percent by weight of such optional or selected ingredient.

The exemplary nutritional compositions, methods of use, and manufacturing methods described or otherwise suggested herein can comprise, consist of, or consist essentially of the elements and limitations disclosed herein, as well as any additional or optional ingredients, components, or limitations disclosed herein or otherwise useful in the nutritional compositions.

Nutritional Composition Form

The nutritional compositions of the present disclosure include at least protein in combination with sequestered calcium HMB, ion-exchanged calcium HMB, or both sequestered calcium HMB and ion-exchanged calcium HMB as described herein, and optionally an inhibitor of electrolyte absorption. The nutritional compositions may be in the form of a liquid, semi-liquid, solid, semi-solid, powder, or bar. In many embodiments, the nutritional composition is in the form of a liquid nutritional emulsion.

The nutritional emulsions of the present disclosure are aqueous emulsions that, in some embodiments, comprise protein, fat, and carbohydrate. These emulsions are flowable or drinkable liquids at from about 1 to about 25° C. and are typically in the form of oil-in-water, water-in-oil, or complex aqueous emulsions, although such emulsions are most typically in the form of oil-in-water emulsions having a continuous aqueous phase and a discontinuous oil phase.

The nutritional emulsions may be and typically are shelf-stable. The nutritional emulsions typically contain up to about 95% of water by weight of the nutritional emulsion, including from about 50% to about 95%, also including from about 60% to about 90%, and also including from about 70% to about 85%, of water by weight of the nutritional emulsion.

The nutritional emulsions may be formulated with sufficient kinds and amounts of nutrients so as to provide a sole, primary, or supplemental source of nutrition, or to provide a specialized nutritional emulsion for use in individuals afflicted with specific diseases or conditions. These nutritional emulsions may thus have a variety of product densities, but most typically have a density greater than about 1.055 g/mL, including from about 1.06 g/ml to about 1.12 g/ml, and including from about 1.085 g/ml to about 1.10 g/ml.

The nutritional emulsions may have a caloric density tailored to the nutritional needs of the ultimate user, although in most instances the emulsions comprise from about 100 kcal/240 ml to about 500 kcal/240 ml, including from about 150 kcal/240 ml to about 350 kcal/240 ml, and including from about 200 kcal/240 ml to about 320 kcal/240 ml. These nutritional emulsions also comprise HMB as described herein, the amount of which most typically ranges from about 0.4 g/240 ml to about 3.0 g/240 ml, including from about 0.75 g/240 ml to about 2.0 g/240 ml, and including about 1.5 g/240 ml. The nutritional emulsions may also, in some embodiments, comprise about 5 g/240 ml to about 30 g/240 ml of protein, including from about 5 g/240 ml to about 20 g/240 ml of protein, and including about 18 g/240 ml of protein, in combination with the HMB.

The nutritional emulsion may have a pH ranging from about 3 to about 8, but are most advantageously in a range of from about 4.5 to about 7.5, including from about 5.5 to about 7.3, and including from about 6.2 to about 7.2.

Although the serving size for the nutritional emulsion can vary depending upon a number of variables, a typical serving size ranges from about 100 ml to about 300 ml, including from about 150 ml to about 250 ml, and including from about 190 ml to about 240 ml.

Sequestered Calcium HMB

In some exemplary embodiments, the nutritional compositions include a sequestered (chelated) calcium HMB in combination with at least one protein or protein source and any other optional ingredients, such as an inhibitor of electrolyte absorption, carbohydrate, fat, vitamins, minerals, etc. The term "sequestered calcium HMB" as used herein, unless otherwise specified, refers to calcium HMB that, prior to incorporation into the nutritional composition, has been subjected to and reacted with a food grade sequestering agent as disclosed, described, or otherwise suggested herein such that at least a portion, and desirably more than 30% by weight, or even about 40% by weight, or even about 50% by weight, or even about 60% by weight, or even about 70% by weight, or even about 80% by weight, or even about 90% by weight, or even about 95% by weight, or even about 97% by weight, or even about 99% by weight, or even 100% by weight of the divalent calcium species present in the calcium HMB is coordinated/chelated/bound with a compound to which the calcium has a high affinity such that the calcium ion is bound up and rendered insoluble in solution and not available for other chemical reaction/interaction in solution, such as chemical reaction/interaction with protein species present in the solution. As such, when the calcium HMB is added into the nutritional compositions of the present disclosure, it is already in sequestered, or chelated/protected/bound form. One skilled in the art, based on the disclosure herein and general knowledge, will be able to determine the particular amounts of sequesterant and calcium HMB, as well as the appropriate reaction conditions, suitable to prepare the sequestered (chelated) HMB for inclusion in the nutritional compositions described herein.

This sequestration of the calcium HMB provides a calcium HMB complex that has a significantly reduced amount of divalent calcium species available for solubilizing into a nutritional composition matrix, as compared to unsequestered calcium HMB, as the calcium is coordinated/chelated to the sequestering agent and is not substantially soluble into the product matrix, which is generally water. As such, the undesirable interactions between soluble calcium species and protein and other components present in the nutritional composition matrix are substantially minimized such that the overall stability, shelf life, and viscosity of the nutritional composition is improved.

In some exemplary embodiments, these various improvements are accomplished by using a food grade sequestering agent (chelator) having low levels of sodium and potassium (and potentially calcium and magnesium), without the use of traditional amounts of one or more of sodium citrates, potassium citrates, sodium phosphates, and potassium phosphates, that can add an undesirably high content of potassium, sodium, and phosphorus to the nutritional composition and render it unsuitable for some individuals, such as individuals with chronic kidney dysfunction. In some exemplary embodiments, one or more of sodium citrates, potassium citrates, sodium phosphates, and potassium phosphates may be used in the nutritional compositions in combination with the sequestered calcium HMB, but will suitably be used in reduced amounts as compared to conventional calcium HMB-containing nutritional compositions to limit the contribution of sodium, potassium, and phosphorus to the nutritional composition.

In some exemplary embodiments, the nutritional composition will have a potassium concentration of less than 1500 ppm, including less than 1200 ppm, including less than 1000 ppm, including less than 900 ppm, including less than 800 ppm, including less than 700 ppm, including less than 600 ppm, including less than 500 ppm, including less than 450 ppm, and including less than 400 ppm. In some exemplary embodiments, the potassium concentration of the nutritional composition is from about 300 ppm to about 1500 ppm, including from about 400 ppm to about 900 ppm, including from about 450 ppm to about 800 ppm, including from about 450 ppm to about 700 ppm, including from about 450 ppm to about 600 ppm, including from about 450 ppm to about 550 ppm, including from about 450 ppm to about 500 ppm.

In some exemplary embodiments, the nutritional composition will have a sodium concentration of less than 700 ppm, including less than 600 ppm, including less than 500 ppm, including less than 400 ppm, including less than 350 ppm, including less than 300 ppm, and including less than 250 ppm. In some exemplary embodiments, the sodium concentration of the nutritional composition is from about 100 ppm to about 700 ppm, including from about 300 ppm to about 700 ppm, including from about 350 ppm to about 700 ppm, including from about 350 ppm to about 600 ppm, including from about 350 ppm to about 500 ppm, and including from about 350 ppm to about 450 ppm.

In some exemplary embodiments, the nutritional composition will have a phosphorus concentration of less than 600 ppm, including less than 500 ppm, including less than 400 ppm, including less than 350 ppm, and including less than 300 ppm. In some exemplary embodiments, the phosphorus concentration of the nutritional composition is from about 200 ppm to about 600 ppm, including from about 300 ppm to about 600 ppm, and including from about 400 ppm to about 500 ppm.

In some exemplary embodiments, the sequestered calcium HMB may be the sole source of calcium HMB present in the nutritional composition; that is, all of the HMB present in the nutritional composition comes from the sequestered calcium HMB source. In other exemplary embodiments, the HMB present in the nutritional composition may come from sequestered calcium HMB and calcium HMB that has not been sequestered with a sequestering agent; that is, the HMB may come from one calcium HMB source that has been sequestered and one calcium HMB source that has not been sequestered.

In some exemplary embodiments, the calcium HMB may be suitably sequestered for subsequent incorporation into a protein-containing nutritional composition by introducing the desired amount of calcium HMB and the desired amount of the sequestering agent into water and admixing for a time sufficient to allow the sequestration of the calcium HMB to occur. After the desired time period for the reaction has passed and the sequestered HMB has formed, the sequestered calcium HMB can be recovered (e.g., by a conventional means) and introduced into the nutritional composition. A wide range of temperatures and pH values can be used, as understood by one of ordinary skill in the art, for suitable sequestration of calcium HMB based on the disclosure herein.

The concentration of sequestered calcium HMB, ion-exchanged calcium HMB (discussed below), or both the sequestered calcium HMB and ion-exchanged calcium HMB in the nutritional compositions may range up to about 20%, including up to about 10%, including from about 0.1% to about 8%, including from about 0.2% to about 5.0%, including from about 0.3% to about 3%, and including from about 0.4% to about 1.5%, by weight of the nutritional composition. In some exemplary embodiments, the nutritional composition may include the sequestered calcium HMB, ion-exchanged HMB, or both in an amount of from about 0.5% to about 2.5%, including from about 0.5% to about 2.0%, including from about 0.6% to about 2.0%, including from about 0.7% to about 1.8%, and including from about 0.8% to about 1.5% by weight of the nutritional composition.

Sequestering (Chelating) Agents for Calcium HMB

Multiple food grade calcium sequestering agents (calcium chelating agents) are suitable for use in accordance with the present disclosure to produce the sequestered calcium HMB. Calcium sequestering agents (calcium chelators) are able to bind calcium (typically in a relationship of one to one) in a selective way (i.e., they have a higher affinity for calcium than for other metal ions present in the system). The binding to the calcium species by the sequestering agent is generally performed through carboxylic groups, so, as will be recognized by one of ordinary skill in the art, the pH of the solution can impact the calcium binding.

In some exemplary embodiments, the sequestering agent or agents selected will contain low respective amounts of potassium, sodium, phosphorus, calcium, and magnesium. The selection of the exact sequestering agent is not critical, so long as it is food grade and meets the requirements discussed herein. One or more sequestering agents may also be used simultaneously to provide the sequestered calcium HMB. Set forth below are exemplary, non-limiting, examples of suitable sequestering agents, each of which may be used alone or in any combination.

A. Glycine Sequestering Agent

In one exemplary embodiment, a sequestered calcium HMB suitable for inclusion in the nutritional composition is prepared using glycine, a glycine derivative, or a glycine analog as the sequestering agent to produce a glycine sequestrate or glycine chelate (glycinate) suitable for use in the nutritional composition. Glycine is a non-essential amino acid with a molecular weight of 75 g/mol that is a naturally occurring sequestering agent. When glycine is used as the sequestering agent, a suitable amount of glycine sequesterant is two moles of glycine for each mole of calcium HMB. In addition to the sequestering and related stability benefits that glycine provides the nutritional compositions, an additional benefit of using glycine as the sequestering agent is that it may additionally provide an increased sweet taste to the nutritional compositions. This additional sweetness may be advantageous in many nutritional composition applications as it may reduce the need for use of other sweeteners, including many carbohydrates.

B. Gluconic Acid Sequestering Agent

In another exemplary embodiment, a sequestered calcium HMB suitable for inclusion in the nutritional composition is prepared using gluconic acid (also commonly referred to as dextronic acid or pentahydroxycaproic acid), a gluconic acid derivative, or a gluconic acid analog as the sequestering agent to produce a gluconic acid sequestrate or gluconic acid chelate suitable for use in the nutritional composition. Gluconic acid is a six carbon chain with five hydroxyl groups terminating in a carboxylic acid group and has a molecular weight of 196 g/mol. Gluconic acid has particularly desirable properties for use as a sequestering agent in the present disclosure at it is a polyhydroxycarboxylic acid, with both carboxyl and hydroxyl groups that can react. When gluconic acid is used as the sequestering agent, a suitable amount of gluconic acid is two moles of gluconic acid for each mole of calcium HMB.

Gluconic acid is a strong chelating agent and it is generally desirable to perform the calcium HMB sequestering with gluconic acid at alkaline conditions as the gluconic acid is particularly effective in these conditions and strongly binds the calcium from the calcium HMB such that interaction with protein in the nutritional composition is substantially reduced or eliminated.

C. Alginate Sequestering Agent

In another exemplary embodiment, a sequestered calcium HMB suitable for inclusion in the nutritional composition is prepared using an alginate, an alginate derivative, or an alginate analog as the sequestering agent to produce an alginate sequestrate or alginate chelate suitable for use in the nutritional composition. In some exemplary embodiments, low gelling and/or low viscosity alginates are desirable. In some exemplary embodiments, high calcium binding alginates are desirable. As used herein, the term "alginate" or "alginates," unless other specified, refers to hydrocolloid water soluble biopolymers extracted from brown seaweed. When an alginate is used as the sequestering agent, a suitable amount of alginate is two moles of alginate for each mole of calcium HMB. Suitable alginate sequestering agents are available from FMC Biopolymer (Philadelphia, Pa.).

D. Phytate (Photic Acid) Sequestering Agent

In another exemplary embodiment, a sequestered calcium HMB suitable for inclusion in the nutritional composition is prepared using a phytate, a phytate derivative, or a phytate analog as the sequestering agent to produce a phytate sequestrate or phytate chelate suitable for use in the nutritional composition. Suitable phytates include phytic acid, inositol hexakisphosphate, phytate, phytin, and combinations thereof. Phytate has a very strong binding affinity to a number of minerals, including calcium. Phytate may be desirable in a number of embodiments of the nutritional compositions described herein as it is effective over a wide pH range as compared to other sequestering agents, and may also provide a significant buffering effect in solution, which can be beneficial in some liquid nutritional compositions. When phytate is used as the sequestering agent, a suitable amount of phytate is two moles of phytate for each mole of calcium HMB.

Ion-Exchanged Calcium HMB

In other exemplary embodiments, the calcium HMB may be subjected to a calcium ion-exchange process prior to incorporation into the nutritional composition such that the calcium ion is exchanged with another ion that is less reactive with the protein source in the nutritional composition. The ion-exchange process may utilize an ion-exchange resin, an ion-exchange polymer, or both an ion-exchange resin and an ion-exchange polymer. The ion-exchange resin or ion-exchange polymer is generally an insoluble matrix or support structure that may, for example, be in the form of 1 to 2 mm diameter beads and fabricated from an organic polymer substrate. A suitable material for use in the present disclosure will have a highly developed structure of pores on the surface of which are sites which easily trap and release ions. The trapping of ions, such as the calcium ions from the calcium HMB, takes place only with the simultaneous release of other ions. This occurs when a liquid solution of the calcium HMB has the ion-exchange resin introduced therein at which time an equilibrium state is reached between ions in solution and ions on the resin. Selectivity coefficients for desirable ions can be determined by one of ordinary skill in the art to determine suitable ion-exchange resins, as well as time periods and conditions for the exchange.

In some exemplary embodiments, an ion-exchange resin may be utilized to exchange the calcium ion from the calcium HMB with another ion that is less reactive with the one or more proteins typically present in the nutritional compositions such that the nutritional compositions are more stable and less likely to have precipitation, sedimentation, and stability issues. In one embodiment, hydrogen ions may be exchanged for the calcium ions.

In some exemplary embodiments, the ion-exchanged calcium HMB may be the sole source of calcium HMB present in the nutritional compositions; that is, all of the HMB present in the nutritional compositions comes from the ion-exchanged calcium HMB. In other exemplary embodiments, the HMB present in the nutritional composition may come from an ion-exchanged calcium HMB and calcium HMB that has not been ion-exchanged with an ion exchange resin; that is, the HMB may come from one calcium HMB source that has been ion-exchanged and one calcium HMB source that has not been ion-exchanged.

Inhibitor of Electrolyte Absorption

In some exemplary embodiments, the nutritional compositions may optionally include an anti-nutrient component such as an inhibitor of electrolyte absorption, sometimes referred to an electrolyte depleter. The inhibitor of electrolyte absorption may be particularly suitable in powdered nutritional compositions and solid nutritional compositions such as meal replacement bars, snack bars, and nutrition bars. The inhibitor of electrolyte absorption can be utilized in the nutritional composition to minimize and reduce the absorption of unwanted and undesirable electrolytes in the body, including any one or more of sodium, potassium, and phosphorus, by binding the electrolyte such that it cannot be absorbed into the body. The inhibitor of electrolyte absorption may be particularly useful in nutritional compositions suitable for use by individuals with chronic kidney dysfunction, renal dysfunction, or hyperphosphatemia, as well as individuals that are required to closely monitor and limit their intake of electrolytes such as potassium, sodium, and phosphorus.

Suitable inhibitors of electrolyte absorption include, for example, calcium bicarbonate, calcium acetate, lanthanum carbonate, and combinations thereof. In some exemplary embodiments, calcium acetate may be particularly desirable as it does not promote aluminum absorption. The nutritional compositions may include the inhibitor of electrolyte absorption in an amount of from about 0.01% to about 5%, including from about 0.01% to about 4%, and including from about 0.1% to about 3% by weight of the nutritional composition. In some exemplary embodiments, the nutritional compositions will provide the individual user with from about 750 to about 1500 milligrams per day of the inhibitor of electrolyte absorption. This may be provided in one, two, three, four or more individual doses.

Macronutrients

In some exemplary embodiments, the nutritional compositions of the present disclosure may comprise, in addition to protein and one of sequestered calcium HMB, ion-exchanged calcium HMB, or both sequestered calcium HMB and ion-exchanged calcium HMB, one or more additional macronutrients including fat, carbohydrate, or both fat and carbohydrate. Generally, any source of protein, fat, and carbohydrate that is known or otherwise suitable for use in nutritional compositions may also be suitable for use herein, provided that such macronutrients are also compatible with the elements of the nutritional compositions as defined herein.

Although total concentrations or amounts of the protein, fat, and carbohydrates may vary depending upon the nutritional needs of the intended user, such concentrations or amounts most typically fall within one of the following embodied ranges, inclusive of any other essential protein, fat, and carbohydrate ingredients as described herein.

Protein concentrations range from about 0.5% to about 30%, including from about 1% to about 15%, and including from about 2% to about 10%, by weight of the nutritional composition. In some exemplary embodiments, the protein concentration may be from about 1% to about 30% by weight of the nutritional composition. In some exemplary embodiments, the protein concentration may be from about 1% to about 30% by weight of the nutritional composition, wherein from about 1% to about 20%, including from about 5% to about 20%, including from about 5% to about 15%, including from about 6% to about 14%, including about 14% of the protein concentration is intact pea protein, such as an intact pea protein concentrate.

Fat concentrations may range from about 1% to about 30%, including from about 1% to about 20%, including from about 2% to about 15%, and including from about 4% to about 10%, by weight of the nutritional composition.

Carbohydrate concentrations may range from about 3% to about 65%, including from about 5% to about 40%, including from about 7% to about 30%, and including from about 10% to about 25%, by weight of the nutritional composition.

The level or amount of protein, fat, and carbohydrate in the nutritional compositions may also be characterized in addition to or in the alternative as a percentage of total calories in the nutritional compositions as set forth in the following table.

| Nutrient (% Calories) | Embodiment A | Embodiment B | Embodiment C |
|---|---|---|---|
| Carbohydrate | 1-98 | 10-75 | 30-50 |
| Fat | 1-98 | 20-85 | 25-50 |
| Protein | 1-98 | 5-70 | 15-35 |

Non-limiting examples of suitable fats or sources thereof for use in the nutritional compositions described herein include coconut oil; fractionated coconut oil; soy oil; corn oil; olive oil; safflower oil; high oleic safflower oil; medium chain triglycerides (MCT) oil; sunflower oil; high oleic sunflower oil; palm and palm kernel oils; palm olein; canola oil; marine oils; cottonseed oils; polyunsaturated fatty acids such as docosahexaenoic acid (DHA), arachidonic acid (ARA), eicosapentaenoic acid (EPA); and combinations thereof. In one exemplary embodiment, the fat system for a nutritional composition includes at least one polyunsaturated fatty acid. In some exemplary embodiments, the at least one polyunsaturated fatty acid is selected from the group consisting of DHA, ARA, EPA, and combinations thereof.

Non-limiting examples of suitable carbohydrates or sources thereof for use in the nutritional compositions described herein may include maltodextrin, hydrolyzed or modified starch or cornstarch, glucose polymers, corn syrup, corn syrup solids, rice-derived carbohydrates, glucose, fructose, lactose, high fructose corn syrup, tapioca dextrin, isomaltulose, soluble dietary fibers such as digestion resistant maltodextrins such as Fibersol® 2 (available from ADM and Matsutani America, Inc.), which is a digestion resistant corn maltodextrin, sucromalt, maltitol powder, glycerin, fructooligosaccharides, soy fiber, corn fiber, guar gum, konjac flour, polydextrose, honey, sugar alcohols (e.g., maltitol, erythritol, sorbitol), and combinations thereof. In one exemplary embodiment, a carbohydrate system for a nutritional composition may include corn maltodextrin and sucrose. In another exemplary embodiment, a carbohydrate system for a nutritional composition may include corn maltodextrin and fructose.

Non-limiting examples of suitable protein or sources thereof for use in the nutritional compositions include one or more of hydrolyzed, partially hydrolyzed or non-hydrolyzed proteins or protein sources, which may be derived from any known or otherwise suitable source such as milk (e.g., casein, whey), animal (e.g., meat, fish), cereal (e.g., rice, corn), vegetable (e.g., soy, pea) or combinations thereof. Non-limiting examples of such proteins or sources thereof include intact pea protein, intact pea protein isolates, intact pea protein concentrates, milk protein isolates, milk protein concentrates, casein protein isolates, casein protein concentrates, whey protein concentrates, whey protein isolates, sodium or calcium caseinates, whole cow's milk, partially or completely defatted milk, soy protein isolates, soy protein concentrates, and combinations thereof.

In one exemplary embodiment, a protein system for a nutritional composition may include sodium caseinate, milk protein concentrate, and soy protein isolate.

In another exemplary embodiment, a protein system for a nutritional composition may include sodium caseinate and calcium caseinate.

In another exemplary embodiment, a protein system for a nutritional composition may include intact pea protein, milk protein concentrate, and soy protein isolate.

In another exemplary embodiment, a protein system for a nutritional composition may include intact pea protein concentrate, soy protein isolate, and milk protein concentrate, wherein the intact pea protein concentrate comprises from about 1% to about 20%, from about 5% to about 20%, from about 5% to about 15%, from about 6% to about 14%, or from about 14% by weight of the protein system; and the milk protein concentrate comprises from about 50% to about 80%, from about 60% to about 70%, from about 60% to about 65% by weight of the protein system; and the soy protein isolate comprises from about 5% to about 40%, or from about 15% to about 25%, as well as about 26% of the protein system.

Soluble Protein

The nutritional compositions of the present disclosure may comprise selected amounts or ratios of "soluble protein" as defined herein to improve their product stability and minimize the development of bitter flavors and after taste during their shelf life.

In some exemplary embodiments, the soluble protein may represent from about 50% to about 100%, including from about 55% to about 100%, including from about 60% to about 100%, including from about 60% to about 85%, including from about 60% to about 80%, and including from about 65% to about 75%, by weight of the total protein in the nutritional composition. The concentration of soluble protein may range from at least about 0.5%, including from about 1% to about 26%, including from about 2% to about 15%, including from about 3% to about 10%, and including from about 4% to about 8%, by weight of the nutritional composition.

The amount of soluble protein included in the nutritional compositions may also be characterized as a weight ratio of soluble protein to sequestered calcium HMB or ion-exchanged calcium HMB, wherein the nutritional composition includes a weight ratio of soluble protein to sequestered calcium HMB, ion-exchanged calcium HMB, or both sequestered calcium HMB and ion-exchanged calcium HMB of at least about 3, including from about 4 to about 12, including from about 6.1 to about 12, including from about 7 to about 11, and including from about 8 to about 10.

The term "soluble protein" as used herein, unless otherwise specified, refers to those proteins having a solubility of at least about 90% as measured in accordance with a Protein Solubility Measurement Test that includes the following steps: (1) suspend the protein at 2.00% (w/w) in water; (2) stir vigorously for one hour at 20° C. to form a suspension; (3) remove an aliquot of the suspension, and determine protein concentration as total protein; (4) centrifuge the suspension at 31,000×g and at 20° C. for one hour; (5) determine the protein concentration in the supernatant (the soluble protein); and (6) express the soluble protein as a percentage of the total protein.

Any soluble protein source is suitable for use herein provided that it meets the solubility requirement as defined herein, some non-limiting examples of which include sodium caseinate (>95% solubility as determined by the Protein Solubility Measurement Test), whey protein concentrate (>90% solubility as determined by the Protein Solubility Measurement Test), and combinations thereof. Non-soluble proteins may of course also be included in the nutritional emulsions provided that the remaining soluble protein component is represented in accordance with the requirements as set forth herein.

Soluble protein suitable for use herein may also be characterized by the content of phosphoserine in the protein, wherein the soluble proteins in this context are defined as those proteins having at least about 100 mmol, including from about 150 mmol to about 400 mmol, including from about 200 mmol to about 350 mmol, and including from about 250 mmol to about 350 mmol of phosphoserine per kilogram of protein.

When the soluble protein is defined in terms of phosphoserine content, it has been found that the weight ratio of the soluble protein (with the defined phosphoserine content) to the calcium HMB may be at least about 3:1, including at least about 5:1, including at least about 7:1, and also including from about 9:1 to about 30:1. In this context, the proteins having the requisite content of phosphoserine are most typically in the form of monovalent caseinate salts such as sodium caseinate, potassium caseinate, and combinations thereof.

In one embodiment, the soluble protein may also be characterized by a mole ratio of monovalent caseinate phosphoserine to calcium HMB of least about 0.2, including from about 0.2 to about 2, and including from about 0.25 to about 1.7.

It should be understood, however, that any phosphoserine-containing protein may be suitable for use herein provided that it has the requisite phosphoserine content and that the phosphoserine used in calculating the ratios are not bound, complexed, or otherwise attached to a polyvalent cation such as calcium or magnesium.

It should also be noted that alternative definitions as described herein for soluble proteins may include proteins that have little or no phosphoserine content, so that the soluble protein fraction of the compositions may include soluble protein with or without phosphoserine. The soluble protein for use herein may therefore be defined by any one or more of the soluble protein characterizations, separately or in combination.

The phosphoserine moieties within the protein may therefore be available for binding with the calcium released from the calcium HMB so that the above ratios of soluble protein to calcium HMB are the ratio of protein with phosphoserine moieties that are unbound, unattached, or otherwise available to bind soluble calcium from the calcium HMB during formulation. It could be, for example, that a mixture of calcium caseinate and sodium caseinate are used in the composition, but the ratio of proteins defined by a phosphoserine content to calcium HMB is calculated based on the protein fraction from the sodium caseinate and additionally any protein from the calcium caseinate fraction that is not bound to calcium.

Soluble Calcium Binding Capacity

The nutritional compositions may comprise a selected weight ratio of a soluble calcium binding capacity (SCBC) to the total soluble calcium in a nutritional emulsion to improve product stability and minimize the development over time of bitter flavors and after taste.

The ratio of the soluble calcium binding capacity (defined herein) to total soluble calcium of the nutritional compositions is a weight ratio of at least about 2.3, including from about 2.3 to about 12, including from about 3 to about 8, and including from about 4 to about 6.5, wherein the ratio is determined in accordance with the following formulas:

Ratio=SCBC/[soluble calcium]

SCBC=(0.32×[soluble citrate]+0.63[soluble phosphate]+0.013×[soluble protein])

The weight ratio of SCBC to the concentration of total soluble calcium can be adjusted to minimize the concentration of unbound calcium in the nutritional composition, or to minimize the weight ratio of such unbound calcium to HMB in the emulsions, to improve product stability and reduce the development over time of bitter flavors and after tastes.

The nutritional compositions of the present disclosure comprise calcium as a desirable ingredient in the nutritional compositions suitable for use in developing or maintaining healthy muscle in targeted individuals. Some or all of the calcium may be provided by the addition of calcium HMB as described herein. Any other calcium source, however, may be used provided that such other source is compatible with the elements of the nutritional compositions described or otherwise suggested herein.

In some exemplary embodiments, the concentration of calcium in the nutritional compositions may be about 10 mg/L, and may also include concentrations of from about 25 mg/L to about 3000 mg/L, from about 50 mg/L to about 500 mg/L, and from about 100 mg/L to about 300 mg/L.

To minimize the taste and stability issues in the nutritional compositions, the calcium is formulated so as to minimize the extent to which the calcium is solubilized in the emulsions. As such, solubilized calcium concentrations in the nutritional compositions may be less than about 900 mg/L, including less than about 700 mg/L, including from about 500 mg/L to about 700 mg/L, and including from about 400 mg/L to about 600 mg/L. In this context, the term "solubilized calcium" refers to free, ionized, or supernatant calcium in the nutritional emulsion as measured at 20° C.

The calcium in the nutritional compositions may also be characterized by a ratio (on an equivalents basis) of solubilized citrate to solubilized calcium of not more than about 5, including not more than about 4, also including not more than about 3, and including from about 0.8 to about 3. In this context, the terms "solubilized citrate" and "solubilized calcium" refer to the equivalents of citrate and calcium cations, respectively, present in the supernatants of the nutritional composition as measured at 20° C.

The calcium component of the nutritional compositions may also be characterized by a solubilized calcium level that represents less than about 900 mg/L, including less than about 700 mg/L, including less than about 600 mg/L, and including from about 400 mg/L to about 700 mg/L of the nutritional emulsion, wherein the weight ratio of calcium HMB to the solubilized calcium ranges from about 6 to about 15, including from about 6 to about 12, including from about 6 to about 10, and including from about 6 to about 8.

Vitamin D

The nutritional compositions of the present disclosure may further comprise vitamin D to help maintain healthy muscle in the targeted user. Vitamin D forms include Vitamin D2 (ergocalciferol) and Vitamin D3 (cholecalciferol), as well as other forms suitable for use in a nutritional composition.

The amount of Vitamin D in the nutritional composition typically ranges up to about 1000 IU, including from about 10 IU to about 600 IU, and including from about 50 IU to 400 IU, per serving of the nutritional composition.

Optional Ingredients

The nutritional compositions described herein may further comprise other optional ingredients that may modify the physical, chemical, hedonic or processing characteristics of the nutritional compositions or serve as pharmaceutical or additional nutritional components when used in the targeted population. Many such optional ingredients are known or otherwise suitable for use in other nutritional compositions and may also be used in the nutritional compositions described herein, provided that such optional ingredients are safe and effective for oral administration and are compatible with the other ingredients in the selected product form.

Non-limiting examples of such optional ingredients include preservatives; antioxidants; emulsifying agents; buffers; pharmaceutical actives; additional nutrients; colorants; flavors; prebiotics such as oligofructose, fructooligosaccharide, galactooligosaccharide, inulin, and combinations thereof; probiotics; beta alanine; functional amino acids such as leucine, valine, isoleucine, or combinations thereof (optionally in free acid form); carotenoids such as for example lutein, including trans-lutein; epigallocatechin gallate dried fruit solid extracts such as plum extracts; curcumin; highly bioavailable curcumin; Salacia extract; cereal beta glucans such as barley beta glucan; thickening agents or stabilizers, and so forth.

The nutritional compositions may further comprise vitamins or related nutrients, non-limiting examples of which include vitamin A, vitamin E, vitamin K, thiamine, riboflavin, pyridoxine, vitamin B12, niacin, folic acid, pantothenic acid, biotin, vitamin C, choline, inositol, salts, and derivatives thereof, and combinations thereof.

The nutritional compositions may further comprise minerals, non-limiting examples of which include phosphorus, magnesium, iron, zinc, manganese, copper, sodium, potassium, molybdenum, chromium, selenium, chloride, and combinations thereof, as long as they are compatible with the elements of the nutritional compositions described or otherwise suggested herein.

The nutritional compositions may also include one or more masking agents to reduce or otherwise obscure the development of any residual bitter or off flavors and after taste in the compositions over time. Suitable masking agents include natural and artificial sweeteners, sodium sources such as sodium chloride, and hydrocolloids, such as guar gum, xanthan gum, carrageenan, gellan gum, and combinations thereof. The amount of masking agent in the nutritional compositions may vary depending upon the particular masking agent selected, other ingredients in the formulation, and other formulation or product target variables. Such amounts, however, most typically range from at least about 0.1%, including from about 0.15% to about 3%, and including from about 0.18% to about 2.5%, by weight of the nutritional composition.

Methods of Manufacture

The nutritional compositions described herein may be manufactured, for example, using conventional methods. Nutritional compositions as described herein in the form of nutritional emulsions may be manufactured by any known or otherwise suitable method for making nutritional emulsions, including milk-based nutritional emulsions.

In one suitable manufacturing process, at least three separate slurries are prepared, including a protein-in-fat (PIF) slurry, a carbohydrate-mineral (CHO-MIN) slurry, and a protein-in-water (PIW) slurry. The PIF slurry is formed by heating and mixing the selected oils (e.g., canola oil, corn oil) and then adding an emulsifier (e.g., lecithin), fat soluble vitamins, and a portion of the total protein (e.g., milk protein concentrate) with continued heat and agitation. The CHO-MN slurry is formed by adding with heated agitation to water: minerals (e.g., potassium citrate, dipotassium phosphate, sodium citrate), trace and ultra trace minerals (TM/UTM premix), thickening or suspending agents (e.g., Avicel, gellan, carrageenan), and calcium HMB or other HMB source. The resulting CHO-MIN slurry is held for 10 minutes with continued heat and agitation before adding additional minerals (e.g., potassium chloride, magnesium carbonate, potassium iodide, etc.), carbohydrates (e.g., fructooligosaccharide, sucrose, corn syrup). The PIW slurry is then formed by mixing with heat and agitation the remaining protein (e.g., sodium caseinate, soy protein concentrate) into water.

The resulting slurries are then blended together with heated agitation and the pH adjusted to the desired range, typically from 6.6 to 7, after which the composition is subjected to high-temperature short-time (HTST) processing during which the composition is heat treated, emulsified and homogenized, and then allowed to cool. Water soluble vitamins and ascorbic acid are added, the pH is again adjusted to the desired range if necessary, flavors are added, and water is added to achieve the desired total solid level. The composition is then aseptically packaged to form an aseptically packaged nutritional emulsion, or the composition is added to retort stable containers and then subjected to retort sterilization to form retort sterilized nutritional emulsions.

The manufacturing processes for the nutritional emulsions may be carried out in ways other than those set forth herein without departing from the spirit and scope of the present disclosure. The disclosed embodiments are, therefore, to be considered in all respects illustrative and not restrictive, and all changes and equivalents relating thereto are encompassed by the general inventive concepts.

Method of Use

The nutritional compositions described herein are useful to provide supplemental, primary, or sole sources of nutrition, and or to provide individuals one or more benefits as described herein. In accordance with methods of using such nutritional compositions, the nutritional compositions may be administered orally as needed to provide the desired level of nutrition, typically in the form of one to two servings daily, in one or two or more divided doses daily. Serving sizes of the nutritional compositions typically range from about 100 ml to about 300 ml, including from about 150 ml to about 250 ml, and including from about 190 ml to about 240 ml, wherein each serving contains from about 0.4 g to about 3 g, including from about 0.75 g to about 2 g, and including about 1.5 g, of calcium HMB per serving.

Such methods, upon administration of such nutritional compositions to an individual, most typically after daily use over an extended period of time ranging from about 1 to about 6 months or from about 1 to about 3 months, are intended to 1) support maintenance of lean body mass, 2) support of strength and or muscle strength, 3) decrease protein breakdown and damage of muscle cells, and 4) help with muscle recovery following exercise or other trauma, 5) reduce muscle protein breakdown following exercise, 6) reduce muscle loss, and 7) combinations thereof.

Such methods are also helpful to achieve one or more of 1) maintaining and supporting lean body mass in elderly with sarcopenia, 2) providing nutrition to support an active and independent lifestyle in individuals, especially in the elderly, 3) supporting recovery of muscle strength, 4) helping rebuild muscle and regain strength, and 5) improving strength, including muscle strength, and mobility.

The nutritional compositions of the present disclosure are suitable for use in reducing muscle loss and promoting muscle mass building in individuals, including individuals such as elderly individuals and individuals with metabolic disorders. As used herein, "metabolic disorders" refers to disorders or defects in the metabolism of an individual, and may be inherited metabolic disorders. Exemplary metabolic disorders in which the nutritional compositions of the present disclosure may be applicable in treating/preventing/reducing include diabetes, chronic kidney dysfunction, end stage renal failure, and the like. Because the exemplary nutritional compositions disclosed herein include protein and calcium HMB and have been stabilized without the need for substantial amounts of sodium citrates, potassium citrates, potassium phosphates or potassium citrates, the nutritional compositions may be particularly beneficial for use in one or more of reducing muscle loss, building or promoting muscle mass building, maintaining muscle mass, and combinations thereof in individuals with one or more of a metabolic disorder, diabetes, chronic kidney dysfunction, and end stage renal failure as the nutritional compositions contain very low levels of electrolytes.

In accordance with the methods disclosed herein, a method of reducing muscle loss in an individual with a metabolic disorder is provided. An exemplary method comprises administering to the individual with the metabolic disorder a liquid nutritional composition comprising calcium beta-hydroxy-beta-methylbutyrate, protein, potassium in a concentration of less than 800 ppm, sodium in a concentration of less than 400 ppm, and phosphorus in a concentration of less than 500 ppm. In other words, a liquid nutritional composition comprising calcium beta-hydroxy-beta-methylbutyrate, protein, potassium in a concentration of less than 800 ppm, sodium in a concentration of less than 400 ppm, and phosphorus in a concentration of less than 500 ppm is for use in reducing muscle loss in an individual with a metabolic disorder.

In accordance with the methods disclosed herein, a method of reducing muscle loss in an individual with diabetes is provided. An exemplary method comprises administering to the individual with diabetes a liquid nutritional composition comprising calcium beta-hydroxy-beta-methylbutyrate, protein, potassium in a concentration of less than 800 ppm, sodium in a concentration of less than 400 ppm, and phosphorus in a concentration of less than 500 ppm. In other words, a liquid nutritional composition comprising calcium beta-hydroxy-beta-methylbutyrate, protein, potassium in a concentration of less than 800 ppm, sodium in a concentration of less than 400 ppm, and phosphorus in a concentration of less than 500 ppm is for use in reducing muscle loss in an individual with diabetes.

In accordance with the methods disclosed herein, a method of reducing muscle loss in an individual with chronic kidney dysfunction is provided. An exemplary method comprises administering to the individual with chronic kidney dysfunction a liquid nutritional composition comprising calcium beta-hydroxy-beta-methylbutyrate, protein, potassium in a concentration of less than 800 ppm, sodium in a concentration of less than 400 ppm, and phosphorus in a concentration of less than 500 ppm. In other words, a liquid nutritional composition comprising calcium beta-hydroxy-beta-methylbutyrate, protein, potassium in a concentration of less than 800 ppm, sodium in a concentration of less than 400 ppm, and phosphorus in a concentration of less than 500 ppm is for use in reducing muscle loss in an individual with chronic kidney dysfunction.

EXAMPLES

The following examples illustrate exemplary embodiments and features of the nutritional compositions of the present disclosure. The examples are given solely for the purpose of illustration and are not to be construed as limitations of the present disclosure, as variations thereof are possible without departing from the spirit and scope of the disclosure. All exemplified amounts are weight percentages based upon the total weight of the formulation, unless otherwise specified.

Examples 1-4

Examples 1-4 illustrate nutritional emulsions of the present disclosure, the ingredients of which are listed in the table below. All ingredient amounts are listed as kilogram per 1000 kilogram batch of product, unless otherwise specified.

| Ingredient | Example 1 | Example 2 | Example 3 | Example 4 |
|---|---|---|---|---|
| Water | Q.S | Q.S. | Q.S. | Q.S. |
| Maltodextrin DE 9-12 | 120.0 | 120.0 | 120.0 | 120.0 |
| Sucrose | 71.38 | 71.38 | 71.38 | 71.38 |
| Milk Protein Concentrate | 18.65 | 18.65 | 18.65 | 18.65 |
| Canola Oil | 27.5 | 27.5 | 27.5 | 27.5 |
| Sodium Caseinate | 26.68 | 26.68 | 26.68 | 26.68 |
| Soy Protein Concentrate | 14.05 | 14.05 | 14.05 | 14.05 |
| Corn Oil | 15.70 | 15.70 | 15.70 | 15.70 |
| Phytate Sequestered Calcium HMB | 6.00 | 6.5 | 7.0 | 4 |
| Calcium bicarbonate | 1.9 | 2.1 | 2.5 | 3.9 |
| Whey Protein Concentrate | 3.50 | 3.50 | 3.50 | 3.50 |
| Magnesium Phosphate | 1.92 | 1.92 | 1.92 | 1.92 |
| Potassium Citrate | 6.92 | 6.92 | 6.92 | 6.92 |
| Sodium Citrate | 0.903 | 0.903 | 0.903 | 0.903 |
| Lecithin | 1.50 | 1.50 | 1.50 | 1.50 |
| Sodium Tripolyphosphate | 1.06 | 1.06 | 1.06 | 1.06 |
| Potassium Phosphate dibasic | 0.730 | 0.730 | 0.730 | 0.730 |
| Potassium Chloride | 1.04 | 1.04 | 1.04 | 1.04 |
| Ascorbic Acid | 0.235 | 0.235 | 0.235 | 0.235 |
| Carrageenan | 0.150 | 0.150 | 0.150 | 0.150 |
| Potassium Hydroxide | 0.136 | 0.136 | 0.136 | 0.136 |
| TM/UTM Premix | 0.1684 | 0.1684 | 0.1684 | 0.1684 |
| Gellan Gum | 0.050 | 0.050 | 0.050 | 0.050 |
| Vitamin A, D, E Premix | 0.0758 | 0.0758 | 0.0758 | 0.0758 |
| Water sol. Vitamin premix | 0.0728 | 0.0728 | 0.0728 | 0.0728 |
| Potassium Iodide | 0.00022 | 0.00022 | 0.00022 | 0.00022 |
| Chromium Chloride | 0.000217 | 0.000217 | 0.000217 | 0.000217 |
| Flavor | 3.3 | 3.3 | 3.3 | 3.3 |

Examples 5-8

Examples 5-8 illustrate nutritional emulsions of the present disclosure, the ingredients of which are listed in the table below. All ingredient amounts are listed as kg per 1000 kg batch of product, unless otherwise specified.

| Ingredient | Example 5 | Example 6 | Example 7 | Example 8 |
| --- | --- | --- | --- | --- |
| Water | Q.S | Q.S. | Q.S. | Q.S. |
| Maltodextrin DE 9-12 | 120.0 | 120.0 | 120.0 | 120.0 |
| Sucrose | 71.38 | 71.38 | 71.38 | 71.38 |
| Milk Protein Concentrate | 14.65 | 13.65 | 12.65 | 11.65 |
| Canola Oil | 27.5 | 27.5 | 27.5 | 27.5 |
| Sodium Caseinate | 30.68 | 31.68 | 32.68 | 33.68 |
| Soy Protein Concentrate | 14.05 | 14.05 | 14.05 | 14.05 |
| Corn Oil | 15.70 | 15.70 | 15.70 | 15.70 |
| Alginate Sequestered Calcium HMB | 6.00 | 6.5 | 7.0 | 7.5 |
| Calcium Acetate | 1.9 | 2.5 | 3.0 | 3.9 |
| Whey Protein Concentrate | 3.50 | 3.50 | 3.50 | 3.50 |
| Magnesium Phosphate | 1.92 | 1.92 | 1.92 | 1.92 |
| Potassium Citrate | 6.92 | 6.92 | 6.92 | 6.92 |
| Sodium Citrate | 0.903 | 0.903 | 0.903 | 0.903 |
| Lecithin | 1.50 | 1.50 | 1.50 | 1.50 |
| Sodium Tripolyphosphate | 1.06 | 1.06 | 1.06 | 1.06 |
| Potassium Phosphate dibasic | 0.730 | 0.730 | 0.730 | 0.730 |
| Potassium Chloride | 1.04 | 1.04 | 1.04 | 1.04 |
| Ascorbic Acid | 0.235 | 0.235 | 0.235 | 0.235 |
| Carrageenan | 0.150 | 0.150 | 0.150 | 0.150 |
| Potassium Hydroxide | 0.136 | 0.136 | 0.136 | 0.136 |
| TM/UTM Premix | 0.1684 | 0.1684 | 0.1684 | 0.1684 |
| Gellan Gum | 0.050 | 0.050 | 0.050 | 0.050 |
| Vitamin A, D, E Premix | 0.0758 | 0.0758 | 0.0758 | 0.0758 |
| Water sol. Vitamin premix | 0.0728 | 0.0728 | 0.0728 | 0.0728 |
| Potassium Iodide | 0.00022 | 0.00022 | 0.00022 | 0.00022 |
| Chromium Chloride | 0.000217 | 0.000217 | 0.000217 | 0.000217 |
| Flavor | 3.3 | 3.3 | 3.3 | 3.3 |

Examples 9-12

Examples 9-12 illustrate nutritional emulsions of the present disclosure, the ingredients of which are listed in the table below. All ingredient amounts are listed as kilogram per 1000 kilogram batch of product, unless otherwise specified.

| Ingredient | Example 9 | Example 10 | Example 11 | Example 12 |
| --- | --- | --- | --- | --- |
| Water | Q.S | Q.S. | Q.S. | Q.S. |
| Maltodextrin DE 9-12 | 120.0 | 120.0 | 120.0 | 120.0 |
| Sucrose | 71.38 | 71.38 | 71.38 | 71.38 |
| Milk Protein Concentrate | 0.00 | 0.00 | 8.65 | 10.65 |
| Canola Oil | 27.5 | 27.5 | 27.5 | 27.5 |
| Sodium Caseinate | 45.33 | 45.33 | 36.68 | 34.68 |
| Soy Protein Concentrate | 0.00 | 0.00 | 12.05 | 9.05 |
| Corn Oil | 15.70 | 15.70 | 15.70 | 15.70 |
| Glycine Sequestered Calcium HMB | 6.0 | 6.5 | 7.0 | 8.0 |
| Calcium Bicarbonate | 1.9 | 2.5 | 3.0 | 3.5 |
| Whey Protein Concentrate | 17.55 | 17.55 | 5.50 | 8.50 |
| Magnesium Phosphate | 1.92 | 1.92 | 1.92 | 1.92 |
| Potassium Citrate | 6.92 | 6.92 | 6.92 | 6.92 |
| Sodium Citrate | 0.903 | 0.903 | 0.903 | 0.903 |
| Lecithin | 1.50 | 1.50 | 1.50 | 1.50 |
| Sodium Tripolyphosphate | 1.06 | 1.06 | 1.06 | 1.06 |
| Potassium Phosphate dibasic | 0.730 | 0.730 | 0.730 | 0.730 |
| Potassium Chloride | 1.04 | 1.04 | 1.04 | 1.04 |
| Ascorbic Acid | 0.235 | 0.235 | 0.235 | 0.235 |
| Carrageenan | 0.150 | 0.150 | 0.150 | 0.150 |
| Potassium Hydroxide | 0.136 | 0.136 | 0.136 | 0.136 |
| TM/UTM Premix | 0.1684 | 0.1684 | 0.1684 | 0.1684 |
| Gellan Gum | 0.050 | 0.050 | 0.050 | 0.050 |
| Vitamin A, D, E Premix | 0.0758 | 0.0758 | 0.0758 | 0.0758 |
| Water sol. Vitamin premix | 0.0728 | 0.0728 | 0.0728 | 0.0728 |
| Potassium Iodide | 0.00022 | 0.00022 | 0.00022 | 0.00022 |
| Chromium Chloride | 0.000217 | 0.000217 | 0.000217 | 0.000217 |
| Flavor | 3.3 | 3.3 | 3.3 | 3.3 |

Examples 13-16

Examples 13-16 illustrate nutritional emulsions of the present disclosure, the ingredients of which are listed in the table below. All ingredient amounts are listed as kilogram per 1000 kilogram batch of product, unless otherwise specified.

| Ingredient | Example 13 | Example 14 | Example 15 | Example 16 |
| --- | --- | --- | --- | --- |
| Water | Q.S | Q.S. | Q.S. | Q.S. |
| Sucrose | 96.05 | 96.05 | 96.05 | 96.05 |
| Maltodextrin DE 5 | 16.46 | 16.46 | 16.46 | 16.46 |
| Milk Protein Concentrate | 18.95 | 0.00 | 8.95 | 25.00 |
| Soy Oil | 13.31 | 13.31 | 13.31 | 13.31 |
| Fructooligosaccharides | 8.69 | 8.69 | 8.69 | 8.69 |
| Soy Protein Concentrate | 13.80 | 0.00 | 10.80 | 5.92 |
| Canola Oil | 5.32 | 5.32 | 5.32 | 5.32 |
| Sodium Caseinate | 25.64 | 58.39 | 61.39 | 28.00 |
| Corn Oil | 11.70 | 11.70 | 11.70 | 11.70 |
| Gluconic Acid Sequestered Calcium HMB | 6.70 | 7.00 | 2.50 | 5.00 |
| Dietary Fiber | 4.51 | 4.51 | 4.51 | 4.51 |
| Whey Protein Concentrate | 3.44 | 3.44 | 13.44 | 2.92 |
| Potassium Citrate | 4.48 | 4.48 | 4.48 | 4.48 |
| Flavor | 2.00 | 2.00 | 2.00 | 2.00 |
| Magnesium Phosphate | 2.75 | 2.75 | 2.75 | 2.75 |
| Lecithin | 1.50 | 1.50 | 1.50 | 1.50 |
| Di sodium Phosphate Dihyd | 0.436 | 0.436 | 0.436 | 0.436 |
| Potassium Phosphate Dibasic | 0.556 | 0.556 | 0.556 | 0.556 |
| Sodium Chloride | 0.498 | 0.498 | 0.498 | 0.498 |
| Choline Chloride | 0.480 | 0.480 | 0.480 | 0.480 |
| Ascorbic Acid | 0.465 | 0.465 | 0.465 | 0.465 |
| Carrageenan | 0.300 | 0.300 | 0.300 | 0.300 |
| Trace/Ultra Trace minerals | 0.420 | 0.420 | 0.420 | 0.420 |
| Potassium Chloride | 0.698 | 0.698 | 0.698 | 0.698 |
| Potassium Hydroxide | 0.321 | 0.321 | 0.321 | 0.321 |
| L-carnitine | 0.180 | 0.180 | 0.180 | 0.180 |
| Water soluble Vitamin Premix | 0.07269 | 0.07269 | 0.07269 | 0.07269 |
| Vitamin DEK premix | 0.128 | 0.128 | 0.128 | 0.128 |
| Gellan Gum | 0.050 | 0.050 | 0.050 | 0.050 |
| Vitamin A Palmitate | 0.008245 | 0.008245 | 0.008245 | 0.008245 |
| Vitamin D3 | 0.000399 | 0.000399 | 0.000399 | 0.000399 |
| Potassium Iodide | 0.000194 | 0.000194 | 0.000194 | 0.000194 |

Examples 17-20

Examples 17-20 illustrate nutritional emulsions of the present disclosure, the ingredients of which are listed in the table below. All ingredient amounts are listed as kilogram per 1000 kilogram batch of product, unless otherwise specified.

| Ingredient | Example 17 | Example 18 | Example 19 | Example 20 |
| --- | --- | --- | --- | --- |
| Water | Q.S | Q.S. | Q.S. | Q.S. |
| Sucrose | 96.05 | 96.05 | 96.05 | 96.05 |
| Maltodextrin DE 5 | 16.46 | 16.46 | 16.46 | 16.46 |
| Milk Protein Concentrate | 24.98 | 0.00 | 25.00 | 10.00 |
| Soy Oil | 13.31 | 13.31 | 13.31 | 13.31 |
| Fructooligosaccharides | 8.69 | 8.69 | 8.69 | 8.69 |
| Soy Protein Concentrate | 13.64 | 0.00 | 5.87 | 10.64 |
| Canola Oil | 5.32 | 5.32 | 5.32 | 5.32 |
| Sodium Caseinate | 25.64 | 58.39 | 61.39 | 28.00 |
| Corn Oil | 11.70 | 11.70 | 11.70 | 11.70 |
| Ion-Exchanged Calcium HMB | 6.50 | 3.5 | 4.25 | 7.5 |
| Dietary Fiber | 4.51 | 4.51 | 4.51 | 4.51 |
| Whey Protein Concentrate | 3.40 | 17.04 | 6.87 | 6.40 |
| Potassium Citrate | 4.48 | 4.48 | 4.48 | 4.48 |
| Flavor | 2.00 | 2.00 | 2.00 | 2.00 |
| Magnesium Phosphate | 2.75 | 2.75 | 2.75 | 2.75 |
| Lecithin | 1.50 | 1.50 | 1.50 | 1.50 |
| Di sodium Phosphate Dihyd | 0.436 | 0.436 | 0.436 | 0.436 |
| Potassium Phosphate Dibasic | 0.556 | 0.556 | 0.556 | 0.556 |
| Sodium Chloride | 0.498 | 0.498 | 0.498 | 0.498 |

-continued

| Ingredient | Example 17 | Example 18 | Example 19 | Example 20 |
|---|---|---|---|---|
| Choline Chloride | 0.480 | 0.480 | 0.480 | 0.480 |
| Ascorbic Acid | 0.465 | 0.465 | 0.465 | 0.465 |
| Carrageenan | 0.300 | 0.300 | 0.300 | 0.300 |
| Trace/Ultra Trace minerals | 0.420 | 0.420 | 0.420 | 0.420 |
| Potassium Chloride | 0.698 | 0.698 | 0.698 | 0.698 |
| Potassium Hydroxide | 0.321 | 0.321 | 0.321 | 0.321 |
| L-carnitine | 0.180 | 0.180 | 0.180 | 0.180 |
| Water soluble Vitamin Premix | 0.07269 | 0.07269 | 0.07269 | 0.07269 |
| Vitamin DEK premix | 0.128 | 0.128 | 0.128 | 0.128 |
| Gellan Gum | 0.050 | 0.050 | 0.050 | 0.050 |
| Vitamin A Palmitate | 0.008245 | 0.008245 | 0.008245 | 0.008245 |
| Vitamin D3 | 0.000399 | 0.000399 | 0.000399 | 0.000399 |
| Potassium Iodide | 0.000194 | 0.000194 | 0.000194 | 0.000194 |

Example 21

In this Example, nutritional emulsions were prepared with varying levels of potassium, with or without the addition of sequestering agents, such as alginate, glycine, or gluconic acid. Various physical and functional properties of the samples were analyzed.

Six nutritional emulsions identified as Samples 1-6 in FIGS. 1A and 1B were prepared having various levels of potassium without the addition of a sequestering agent. Samples 1-6 were formulated according to the formulations shown in the following table.

| Ingredient | Sample 1 Amount (KG/1000 KG Product) | Sample 2 Amount (KG/1000 KG Product) | Sample 3 Amount (KG/1000 KG Product) | Sample 4 Amount (KG/1000 KG Product) | Sample 5 Amount (KG/1000 KG Product) | Sample 6 Amount (KG/1000 KG Product) |
|---|---|---|---|---|---|---|
| Water | QS | QS | QS | QS | QS | QS |
| Fibersol 2 (Corn Maltodextrin) | 91.15 | 91.15 | 91.15 | 91.15 | 40.19 | 40.19 |
| Milk Protein Concentrate | 57.66 | 57.66 | 57.66 | 57.66 | 57.66 | 57.66 |
| Sucromalt | 56.49 | 56.49 | 56.49 | 56.49 | 25.37 | 25.37 |
| Sodium Caseinate | 26.14 | 26.14 | 26.14 | 26.14 | 26.14 | 26.14 |
| Glycerol | 24.90 | 24.90 | 24.90 | 24.90 | 25.00 | 25.00 |
| High Oleic Safflower Oil | 17.25 | 17.25 | 17.25 | 17.25 | 23.69 | 23.69 |
| Fructose | 15.33 | 15.33 | 15.33 | 15.33 | 15.38 | 15.38 |
| Canola Oil | 12.99 | 12.99 | 12.99 | 12.99 | 17.84 | 17.84 |
| Soy Oil | 10.86 | 10.86 | 10.86 | 10.86 | 14.92 | 14.92 |
| Soy Protein Isolate | 9.057 | 9.057 | 9.057 | 9.057 | 9.057 | 9.057 |
| Maltrin M100 (Maltodextrin) | 8.117 | 8.117 | 8.117 | 8.117 | 14.52 | 14.52 |
| Calcium HMB | 6.703 | 6.703 | 6.703 | 6.703 | 6.703 | 6.703 |
| Potassium Citrate | 3.579 | 4.500 | 3.579 | 4.500 | 3.579 | 3.579 |
| Magnesium Phosphate Dibasic | 3.100 | 3.100 | 3.100 | 3.100 | 3.100 | 3.100 |
| Disodium Phosphate | 1.500 | 1.500 | 1.500 | 1.500 | 1.500 | 1.500 |
| Soy Lecithin | 1.491 | 1.491 | 1.491 | 1.491 | 2.048 | 2.048 |
| Potassium Phosphate Dibasic, FCC | 0.9868 | 0.9868 | 0.9868 | 0.9868 | 0.9868 | 0.9868 |
| Choline Chloride | 0.4801 | 0.4801 | 0.4801 | 0.4801 | 0.4801 | 0.4801 |
| Ascorbic Acid | 0.4687 | 0.4687 | 0.4687 | 0.4687 | 0.6000 | 0.6000 |
| 45% Potassium Hydroxide | 0.3234 | 0.3234 | 0.3234 | 0.3234 | 0.4140 | 0.4140 |
| Ultra Trace Mineral/Trace Mineral/Water Soluble Vitamin Premix | 0.2717 | 0.2717 | 0.2717 | 0.2717 | 0.2717 | 0.2717 |
| Sodium Chloride | 0.100 | 0.100 | 0.100 | 0.100 | 0.700 | 0.700 |
| Vitamin D, E, K Premix | 0.0675 | 0.0675 | 0.0675 | 0.0675 | 0.0675 | 0.0675 |

-continued

| Ingredient | Sample 1 Amount (KG/1000 KG Product) | Sample 2 Amount (KG/1000 KG Product) | Sample 3 Amount (KG/1000 KG Product) | Sample 4 Amount (KG/1000 KG Product) | Sample 5 Amount (KG/1000 KG Product) | Sample 6 Amount (KG/1000 KG Product) |
|---|---|---|---|---|---|---|
| Vitamin A Palmitate, USP | 0.0082 | 0.0082 | 0.0082 | 0.0082 | 0.0082 | 0.0082 |
| Vitamin D3 | 0.0004 | 0.0004 | 0.0004 | 0.0004 | 0.0004 | 0.0004 |
| Potassium Iodide | 0.00019 | 0.00019 | 0.00019 | 0.00019 | 0.00019 | 0.00019 |
| Vitamin B12 | 0.000016 | 0.000016 | 0.000016 | 0.000016 | 0.000016 | 0.000016 |

Five nutritional emulsions identified as Samples 7-11 in FIGS. 2A and 2B were prepared with approximately 200 mg potassium per 100 g of product and various levels of alginate as a sequestering agent. Samples 7-11 were formulated according to the formulations shown in the following table.

| Ingredient | Sample 7 Amount (KG/1000 KG Product) | Sample 8 Amount (KG/1000 KG Product) | Sample 9 Amount (KG/1000 KG Product) | Sample 10 Amount (KG/1000 KG Product) | Sample 11 Amount (KG/1000 KG Product) |
|---|---|---|---|---|---|
| Water | QS | QS | QS | QS | QS |
| Fibersol 2 (Corn Maltodextrin) | 91.15 | 91.15 | 91.15 | 40.19 | 40.19 |
| Milk Protein Concentrate | 57.66 | 57.66 | 57.66 | 57.66 | 57.66 |
| Sucromalt | 56.49 | 56.49 | 56.49 | 25.37 | 25.37 |
| Sodium Caseinate | 26.14 | 26.14 | 26.14 | 26.14 | 26.14 |
| Glycerol | 24.90 | 24.90 | 24.90 | 25.00 | 25.00 |
| High Oleic Safflower Oil | 17.25 | 17.25 | 17.25 | 23.69 | 23.69 |
| Fructose | 15.33 | 15.33 | 15.33 | 15.38 | 15.38 |
| Canola Oil | 12.99 | 12.99 | 12.99 | 17.84 | 17.84 |
| Soy Oil | 10.86 | 10.86 | 10.86 | 14.92 | 14.92 |
| Soy Protein Isolate | 9.057 | 9.057 | 9.057 | 9.057 | 9.057 |
| Maltrin M100 (Maltodextrin) | 8.117 | 8.117 | 8.117 | 14.52 | 14.52 |
| Calcium HMB | 6.703 | 6.703 | 6.703 | 6.703 | 6.703 |
| Alginate | 5.000 | 5.000 | 2.500 | 0.800 | 1.600 |
| Potassium Citrate | 3.579 | 3.579 | 3.579 | 3.579 | 3.579 |
| Magnesium Phosphate Dibasic | 3.100 | 3.100 | 3.100 | 3.100 | 3.100 |
| Disodium Phosphate | 1.500 | 1.500 | 1.500 | 1.500 | 1.500 |
| Soy Lecithin | 1.491 | 1.491 | 1.491 | 2.048 | 2.048 |
| Potassium Phosphate Dibasic, FCC | 0.9868 | 0.9868 | 0.9868 | 0.9868 | 0.9868 |
| Choline Chloride | 0.4801 | 0.4801 | 0.4801 | 0.4801 | 0.4801 |
| Ascorbic Acid | 0.4687 | 0.4687 | 0.4687 | 0.6000 | 0.6000 |
| 45% Potassium Hydroxide | 0.3234 | 0.3234 | 0.3234 | 0.4140 | 0.4140 |
| Ultra Trace Mineral/Trace Mineral/Water Soluble Vitamin Premix | 0.2717 | 0.2717 | 0.2717 | 0.2717 | 0.2717 |
| Sodium Chloride | 0.1000 | 0.1000 | 0.1000 | 0.7000 | 0.7000 |
| Vitamin D, E, K Premix | 0.0675 | 0.0675 | 0.0675 | 0.0675 | 0.0675 |
| Vitamin A Palmitate, USP | 0.0082 | 0.0082 | 0.0082 | 0.0082 | 0.0082 |
| Vitamin D3 | 0.0004 | 0.0004 | 0.0004 | 0.0004 | 0.0004 |
| Potassium Iodide | 0.00019 | 0.00019 | 0.00019 | 0.00019 | 0.00019 |
| Vitamin B12 | 0.000016 | 0.000016 | 0.000016 | 0.000016 | 0.000016 |

Two nutritional emulsions identified as Samples 12 and 13 in FIGS. 3A and 3B were prepared with 200 mg potassium per 100 g of product and various levels of glycine as a sequestering agent. Seven nutritional emulsions identified as Samples 14-20 in FIGS. 3A and 3B were prepared with 200 mg potassium per 100 g of product and either glucono delta lactone (lactone of d-gluconic acid) or sodium gluconate (sodium salt of gluconic acid), and in certain samples, glycine. Samples 12-20 were formulated according to the formulations shown in the following two tables.

| Ingredient | Sample 12 Amount (KG/1000 KG Product) | Sample 13 Amount (KG/1000 KG Product) | Sample 14 Amount (KG/1000 KG Product) | Sample 15 Amount (KG/1000 KG Product) |
|---|---|---|---|---|
| Water | QS | QS | QS | QS |
| Milk Protein Concentrate (82%) | 57.66 | 57.66 | 57.66 | 57.66 |
| Fibersol 2 (Corn Maltodextrin) | 40.19 | 40.19 | 91.15 | 91.15 |
| Sodium Caseinate | 26.14 | 26.14 | 26.14 | 26.14 |
| Sucromalt | 25.37 | 25.37 | 56.49 | 56.49 |
| Glycerol | 25.00 | 25.00 | 24.90 | 24.90 |
| High Oleic Safflower Oil | 23.69 | 23.69 | 17.25 | 17.25 |
| Canola Oil | 17.84 | 17.84 | 12.99 | 12.99 |
| Fructose | 15.38 | 15.38 | 15.33 | 15.33 |
| Soy Oil | 14.92 | 14.92 | 10.86 | 10.86 |
| Maltrin M100 (Maltodextrin) | 14.52 | 14.52 | 8.117 | 8.117 |
| Fructooligosaccharide (FOS) Powder | 11.74 | 11.74 | — | — |
| Soy Protein Isolate | 9.057 | 9.057 | 9.057 | 9.057 |
| Calcium HMB | 6.703 | 6.703 | 6.703 | 6.703 |
| Potassium Citrate | 3.579 | 3.579 | 3.579 | 3.579 |
| Magnesium Phosphate Dibasic | 3.100 | 3.100 | 3.100 | 3.100 |
| Soy Lecithin | 2.048 | 2.048 | 1.491 | 1.491 |
| Glycine | 2.000 | 4.000 | 1.662 | 3.324 |
| Glucone delta Lactone | — | — | 1.662 | 3.324 |
| Sodium Gluconate | — | — | — | — |
| Disodium Phosphate | 1.500 | 1.500 | 1.500 | 1.500 |
| Potassium Phosphate Dibasic, FCC | 0.9868 | 0.9868 | 0.9868 | 0.9868 |
| Sodium Chloride | 0.7000 | 0.7000 | 0.1000 | 0.1000 |
| Ascorbic Acid | 0.6000 | 0.6000 | 0.4687 | 0.4687 |
| Choline Chloride | 0.4801 | 0.4801 | 0.4801 | 0.4801 |
| 45% Potassium Hydroxide | 0.4140 | 0.4140 | 0.3234 | 0.3234 |
| Ultra Trace Mineral/Trace Mineral/Water Soluble Vitamin Premix | 0.2717 | 0.2717 | 0.2717 | 0.2717 |
| Vitamin D, E, K Premix | 0.0675 | 0.0675 | 0.0675 | 0.0675 |
| Vitamin A Palmitate, USP | 0.0082 | 0.0082 | 0.0082 | 0.0082 |
| Vitamin D3 | 0.0004 | 0.0004 | 0.0004 | 0.0004 |
| Potassium Iodide | 0.00019 | 0.00019 | 0.00019 | 0.00019 |
| Vitamin B12 | 0.000016 | 0.000016 | 0.000016 | 0.000016 |

| Ingredient | Sample 16 Amount (KG/1000 KG Product) | Sample 17 Amount (KG/1000 KG Product) | Sample 18 Amount (KG/1000 KG Product) | Sample 19 Amount (KG/1000 KG Product) | Sample 20 Amount (KG/1000 KG Product) |
|---|---|---|---|---|---|
| Water | QS | QS | QS | QS | QS |
| Milk Protein Concentrate (82%) | 57.66 | 57.66 | 57.66 | 57.66 | 57.66 |
| Fibersol 2 (Corn Maltodextrin) | 91.15 | 91.15 | 91.15 | 91.15 | 91.15 |
| Sodium Caseinate | 26.14 | 26.14 | 26.14 | 26.14 | 26.14 |
| Sucromalt | 56.49 | 56.49 | 56.49 | 56.49 | 56.49 |
| Glycerol | 24.90 | 24.90 | 24.90 | 24.90 | 24.90 |
| High Oleic Safflower Oil | 17.25 | 17.25 | 17.25 | 17.25 | 17.25 |
| Canola Oil | 12.99 | 12.99 | 12.99 | 12.99 | 12.99 |
| Fructose | 15.33 | 15.33 | 15.33 | 15.33 | 15.33 |
| Soy Oil | 10.86 | 10.86 | 10.86 | 10.86 | 10.86 |
| Maltrin M100 (Maltodextrin) | 8.117 | 8.117 | 8.117 | 8.117 | 8.117 |
| Fructooligosaccharide (FOS) Powder | — | — | — | — | — |
| Soy Protein Isolate | 9.057 | 9.057 | 9.057 | 9.057 | 9.057 |
| Calcium HMB | 6.703 | 6.703 | 6.703 | 6.703 | 6.703 |
| Potassium Citrate | 3.579 | 3.579 | 3.579 | 3.579 | 3.579 |
| Magnesium Phosphate Dibasic | 3.100 | 3.100 | 3.100 | 3.100 | 3.100 |
| Soy Lecithin | 1.491 | 1.491 | 1.491 | 1.491 | 1.491 |
| Glycine | 5.011 | 0.508 | 1.015 | 1.523 | 0.000 |
| Glucone delta Lactone | 5.011 | 0.508 | 1.015 | 1.523 | — |
| Sodium Gluconate | — | — | — | — | 3.877 |
| Disodium Phosphate | 1.500 | 1.500 | 1.500 | 1.500 | 1.500 |

-continued

| | | | | | |
|---|---|---|---|---|---|
| Potassium Phosphate Dibasic, FCC | 0.9868 | 0.9868 | 0.9868 | 0.9868 | 0.9868 |
| Sodium Chloride | 0.1000 | 0.1000 | 0.1000 | 0.1000 | 0.1000 |
| Ascorbic Acid | 0.4687 | 0.4687 | 0.4687 | 0.4687 | 0.4687 |
| Choline Chloride | 0.4801 | 0.4801 | 0.4801 | 0.4801 | 0.4801 |
| 45% Potassium Hydroxide | 0.3234 | 0.3234 | 0.3234 | 0.3234 | 0.3234 |
| Ultra Trace Mineral/Trace Mineral/Water Soluble Vitamin Premix | 0.2717 | 0.2717 | 0.2717 | 0.2717 | 0.2717 |
| Vitamin D, E, K Premix | 0.0675 | 0.0675 | 0.0675 | 0.0675 | 0.0675 |
| Vitamin A Palmitate, USP | 0.0082 | 0.0082 | 0.0082 | 0.0082 | 0.0082 |
| Vitamin D3 | 0.0004 | 0.0004 | 0.0004 | 0.0004 | 0.0004 |
| Potassium Iodide | 0.00019 | 0.00019 | 0.00019 | 0.00019 | 0.00019 |
| Vitamin B12 | 0.000016 | 0.000016 | 0.000016 | 0.000016 | 0.000016 |

The samples were tasted by individuals immediately after being prepared. It was found that the off notes typically associated with calcium HMB were lessened with the addition of alginate.

The samples were also evaluated for color, sedimentation, stability, and pH initially after being prepared, and then, again, after 1 month, 3 months, 6 months, and 9 months. Results are shown in FIGS. 1A, 1B, 2A, 2B, 3A, and 3B.

Particularly, the color of the samples were evaluated using an Agtron color analyzer (available as Model M-45 from Agtron, Inc., Reno, Nev.) and using a Hunter Lab analysis. As shown in FIGS. 1A, 2A, and 3A, the color of the emulsion samples including sequestering agents was comparable to the color of samples without. Physical stability, as measured by the samples producing a creaming effect, a gelling effect, grainy effect, and new creaming effect, was also comparable between emulsion samples including sequestering agents and samples without sequestering agents as shown in FIGS. 1A, 1B, 2A, 2B, 3A, and 3B. Grainy effect refers to the level of protein stability. The lower the score in the grainy effect, indicates a higher probability of protein stability.

FIGS. 1A, 1B, 2A, 2B, 3A, and 3B further show that sediment values were lower in the emulsion samples including a sequestering agent. As shown in FIGS. 1B, 2B, and 3B, the pH of the samples was affected when glycine and gluconic acid were included as sequestering agents.

Additionally, the samples were evaluated for their ability to bind to calcium. Particularly, the samples were centrifuged using high speed centrifugation (31,000×g; 20° C.; 2 h). The soluble calcium concentrations, including unbound ("free") calcium and any calcium bound as a soluble salt (e.g., $CaCl_2$) or as a soluble complex (e.g., calcium caseinate) were than measured. The results are shown in FIG. 4.

As shown in FIG. 4, there is an increase in bound calcium with the emulsion samples including the sequestering agents as compared to the samples without sequestering agents.

What is claimed is:

1. A liquid nutritional composition comprising sequestered calcium beta-hydroxy-beta-methylbutyrate, protein, potassium, sodium and phosphorus, wherein the potassium concentration is less than 800 ppm, the sodium concentration is less than 400 ppm, and the phosphorus concentration is less than 500 ppm.

2. The liquid nutritional composition of claim 1, wherein the potassium is in a concentration of less than 500 ppm, the sodium is in a concentration of less than 350 ppm, and the phosphorus is in a concentration of less than 400 ppm.

3. The liquid nutritional composition of claim 1 further comprising fat and carbohydrate.

4. The liquid nutritional composition of claim 3, wherein the fat is selected from the group consisting of high oleic safflower oil, high oleic sunflower oil, canola oil, soy oil, corn oil, and combinations thereof.

5. The liquid nutritional composition of claim 3, wherein the fat includes at least one polyunsaturated fatty acid.

6. The liquid nutritional composition of claim 5, wherein the at least one polyunsaturated fatty acid is selected from the group consisting of docosahexaenoic acid, arachidonic acid, eicosapentaenoic acid, and combinations thereof.

7. The liquid nutritional composition of claim 3, wherein the protein is selected from the group consisting of milk protein concentrate, milk protein isolate, soy protein concentrate, soy protein isolate, intact pea protein concentrate, intact pea protein isolate, sodium caseinate, calcium caseinate, whey protein concentrate, whey protein isolate, and combinations thereof.

8. The liquid nutritional composition of claim 3, wherein the carbohydrate is selected from the group consisting of maltodextrin, corn syrup solids, corn syrup, tapioca dextrin, isomaltulose, digestion resistant maltodextrin, sucromalt, maltitol powder, fructose, glycerin, fructooligosaccharide, soy fiber, corn fiber, guar gum, konjac flour, polydextrose, and combinations thereof.

9. The liquid nutritional composition of claim 3, further comprising a soy fiber.

10. The liquid nutritional composition of claim 3, further comprising a prebiotic.

11. The liquid nutritional composition of claim 10, wherein the prebiotic is selected from the group consisting of oligofructose, fructooligosaccharide, galactooligosaccharide, inulin, and combinations thereof.

12. The liquid nutritional composition of claim 3, comprising protein in an amount of from about 1% to about 30% by weight, carbohydrate in an amount of from about 3% to about 65% by weight, and fat in an amount of from about 1% to about 20% by weight, wherein the protein comprises from about 1% to about 20% by weight intact pea protein.

13. The liquid nutritional composition of claim 12, wherein the protein comprises intact pea protein concentrate, milk protein concentrate, and soy protein isolate.

14. A method of reducing muscle loss in an individual with a metabolic disorder, diabetes, or chronic kidney dysfunction, the method comprising administering a liquid nutritional composition comprising sequestered calcium beta-hydroxy-beta-methylbutyrate, protein, potassium, sodium and phosphorus, wherein the potassium concentration is less than 800 ppm, the sodium concentration is less than 400 ppm, and the phosphorus concentration is less than 500 ppm to the individual with the metabolic disorder, diabetes, or chronic kidney dysfunction.

15. A liquid nutritional composition comprising sequestered calcium beta-hydroxy-beta-methylbutyrate, protein, and potassium, wherein the potassium concentration is less than 800 ppm.

16. The liquid nutritional composition of claim 15, wherein the potassium is in a concentration of from about 300 ppm to about 500 ppm.

17. The liquid nutritional composition of claim 15 further comprising fat and carbohydrate.

18. The liquid nutritional composition of claim 17 comprising protein in an amount of from about 1% to about 30% by weight, carbohydrate in an amount of from about 3% to about 65% by weight, and fat in an amount of from about 1% to about 20% by weight, wherein the protein comprises from about 1% to about 20% by weight intact pea protein.

19. The liquid nutritional composition of claim 1, wherein the sequestered calcium beta-hydroxy-beta-methylbutyrate is at least one of a glycine sequestrate, a gluconic acid sequestrate, an alginate sequestrate, or a phytate sequestrate.

20. The liquid nutritional composition of claim 15, wherein the sequestered calcium beta-hydroxy-beta-methylbutyrate is at least one of a glycine sequestrate, a gluconic acid sequestrate, an alginate sequestrate, or a phytate sequestrate.

21. The liquid nutritional composition of claim 1, wherein the composition has a pH of 5.5 to 7.3.

* * * * *